US009517303B2

(12) United States Patent
Bazargan et al.

(10) Patent No.: US 9,517,303 B2
(45) Date of Patent: Dec. 13, 2016

(54) RESERVOIR PLUNGER POSITION MONITORING AND MEDICAL DEVICE INCORPORATING SAME

(71) Applicant: MEDTRONIC MINIMED, INC., Northridge, CA (US)

(72) Inventors: Afshin Bazargan, Simi Valley, CA (US); Pablo Vazquez, Granada Hills, CA (US); EJMar Fonacier, Woodland Hills, CA (US); Andrew E. Weaver, Granada Hills, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 173 days.

(21) Appl. No.: 14/323,931

(22) Filed: Jul. 3, 2014

(65) Prior Publication Data

US 2014/0324018 A1    Oct. 30, 2014

Related U.S. Application Data

(63) Continuation of application No. 13/591,129, filed on Aug. 21, 2012, now Pat. No. 8,808,269.

(51) Int. Cl.
*A61M 37/00* (2006.01)
*A61M 5/168* (2006.01)
(Continued)

(52) U.S. Cl.
CPC ....... *A61M 5/16831* (2013.01); *A61M 5/1456* (2013.01); *A61M 5/14212* (2013.01);
(Continued)

(58) Field of Classification Search
CPC ............ A61M 5/1684; A61M 5/14212; A61M 5/16831; A61M 5/1685
(Continued)

(56) References Cited

U.S. PATENT DOCUMENTS 2,903,666 A  *  9/1959  Krellner .................. H01C 7/001
                                                      29/619
3,631,847 A      1/1972  Hobbs, II
(Continued)

FOREIGN PATENT DOCUMENTS

DE        4329229        3/1995
EP        0319268        11/1988
(Continued)

OTHER PUBLICATIONS

PCT Search Report (PCT/US02/03299), Oct. 31, 2002, Medtronic Minimed, Inc.
(Continued)

*Primary Examiner* — Edelmira Bosques
(74) *Attorney, Agent, or Firm* — Lorenz & Kopf, LLP

(57) ABSTRACT

Apparatus are provided for infusion devices and related control systems and methods. In one embodiment, an infusion device includes a voided portion adapted to receive a shaft portion that includes a shaft coupled to a plunger of a reservoir. The shaft portion includes a detectable feature, and the infusion device includes a sensing arrangement proximate the voided portion to sense the detectable feature. In some embodiments, a control module is coupled to the sensing arrangement to determine a remaining amount of fluid in the reservoir based at least in part on the sensed position of the detectable feature. In other embodiments, the control module identifies an anomalous condition based at least in part on the sensed position of the detectable feature.

20 Claims, 18 Drawing Sheets

(51) Int. Cl.
*A61M 5/145* (2006.01)
*A61M 5/142* (2006.01)
*A61M 5/172* (2006.01)

(52) U.S. Cl.
CPC ...... *A61M 5/14248* (2013.01); *A61M 5/1684* (2013.01); *A61M 5/1723* (2013.01); *A61M 2005/16863* (2013.01); *A61M 2205/14* (2013.01); *A61M 2205/332* (2013.01); *A61M 2205/3306* (2013.01); *A61M 2205/3317* (2013.01); *A61M 2205/3365* (2013.01); *A61M 2205/6054* (2013.01); *A61M 2205/6063* (2013.01); *A61M 2205/6081* (2013.01)

(58) Field of Classification Search
USPC .................................................. 604/151, 131
See application file for complete search history.

(56) References Cited

U.S. PATENT DOCUMENTS

| | | |
|---|---|---|
| 4,212,738 A | 7/1980 | Henne |
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | DeCant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,176,502 A * | 1/1993 | Sanderson .......... A61M 5/1456 417/18 |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,497,772 A | 3/1996 | Schulman et al. |
| 5,505,709 A | 4/1996 | Funderburk et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Iliff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,704,922 A | 1/1998 | Brown |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |

(56) References Cited

U.S. PATENT DOCUMENTS

| | | |
|---|---|---|
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Plante et al. |
| 6,579,690 B1 | 6/2003 | Bonnecaze et al. |
| 6,589,229 B1 | 7/2003 | Connelly et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,740,072 B2 | 5/2004 | Starkweather et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,817,990 B2 | 11/2004 | Yap et al. |
| 6,827,702 B2 | 12/2004 | Lebel et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,323,142 B2 | 1/2008 | Pendo et al. |
| 7,396,330 B2 | 7/2008 | Banet et al. |
| 7,621,893 B2 | 11/2009 | Moberg et al. |
| 7,828,764 B2 | 11/2010 | Moberg et al. |
| 7,905,868 B2 | 3/2011 | Moberg et al. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0009133 A1 | 1/2003 | Ramey |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0077081 A1* | 3/2008 | Mounce ............... A61M 5/1413 604/67 |
| 2008/0154503 A1 | 6/2008 | Wittenber et al. |
| 2009/0081951 A1 | 3/2009 | Erdmann et al. |
| 2009/0082635 A1 | 3/2009 | Baldus et al. |
| 2011/0233393 A1* | 9/2011 | Hanson .................. G01D 11/30 250/231.14 |
| 2012/0259282 A1 | 10/2012 | Alderete, Jr. et al. |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |
| WO | WO2009/102355 A2 | 8/2009 |

OTHER PUBLICATIONS (Animas Corporation, 1999). Animas . . . bringing new life to insulin therapy.

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

(56) References Cited

OTHER PUBLICATIONS

Brackenridge B P (1992). Carbohydrate Gram Counting A Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting A Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed Jet al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed• Technologies.
(Intensive Diabetes Management, 1995). Insulin Infusion Pump Therapy. pp. 66-78.
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.cornifiles/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump For those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.

Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.

(56) References Cited

OTHER PUBLICATIONS

Moussy, Francis, et al., "Performance of Subcutaneously Implanted Needle-Type Glucose Sensors Employing a Novel Inlayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artificel endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine -co-n-butyl nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.
Reach, G., "A Method for Evaluating in vivo the Functional Characteristics of Glucose Sensors," Biosensors 2, 1986, pp. 211-220.
Shaw, G. W., et al., "In vitro testing of a simply constructed, highly stable glucose sensor suitable for implantation in diabetic patients," Biosensors & Bioelectronics 6, 1991, pp. 401-406.
Shichiri, M., "A Needle-Type Glucose Sensor—A Valuable Tool Not Only For a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.
Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.
Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.
Shichiri, Motoaki, et al., "Glycaemic Control in a Pacreatectomized Dogs with a Wearable Artificial Endocrine Pancreas," Diabetologia, vol. 24, 1983, pp. 179-184.
Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.
Shichiri, M., et al., "Membrane design for extending the long-life of an implantable glucose sensor," Diab. Nutr. Metab., vol. 2, No. 4, 1989, pp. 309-313.
Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.
Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.
Shichiri, Motoaki, et al., "Wearable Artificial Endocrine Pancreas with Needle-Type Glucose Sensor," The Lancet, Nov. 20, 1982, pp. 1129-1131.
Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.
Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.
Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.
Sternberg, Robert, et al., "Study and Development of Multilayer Needle-type Enzyme-based Glucose Microsensors," Biosensors, vol. 4, 1988, pp. 27-40.
Tamiya, E., et al., "Micro Glucose Sensors using Electron Mediators Immobilized on a Polypyrrole-Modified Electrode," Sensors and Actuators, vol. 18, 1989, pp. 297-307.
Tsukagoshi, Kazuhiko, et al., "Specific Complexation with Mono- and Disaccharides that can be Detected by Circular Dichroism," J. Org. Chem., vol. 56, 1991, pp. 4089-4091.
Urban, G., et al., "Miniaturized multi-enzyme biosensors integrated with pH sensors on flexible polymer carriers for in vivo applciations," Biosensors & Bioelectronics, vol. 7, 1992, pp. 733-739.
Ubran, G., et al., "Miniaturized thin-film biosensors using covalently immobilized glucose oxidase," Biosensors & Bioelectronics, vol. 6, 1991, pp. 555-562.
Velho, G., et al., "In vivo calibration of a subcutaneous glucose sensor for determination of subcutaneous glucose kinetics," Diab. Nutr. Metab., vol. 3, 1988, pp. 227-233.
Wang, Joseph, et al., "Needle-Type Dual Microsensor for the Simultaneous Monitoring of Glucose and Insulin," Analytical Chemistry, vol. 73, 2001, pp. 844-847.
Yamasaki, Yoshimitsu, et al., "Direct Measurement of Whole Blood Glucose by a Needle-Type Sensor," Clinics Chimica Acta, vol. 93, 1989, pp. 93-98.
Yokoyama, K., "Integrated Biosensor for Glucose and Galactose," Analytica Chimica Acta, vol. 218, 1989, pp. 137-142.

* cited by examiner

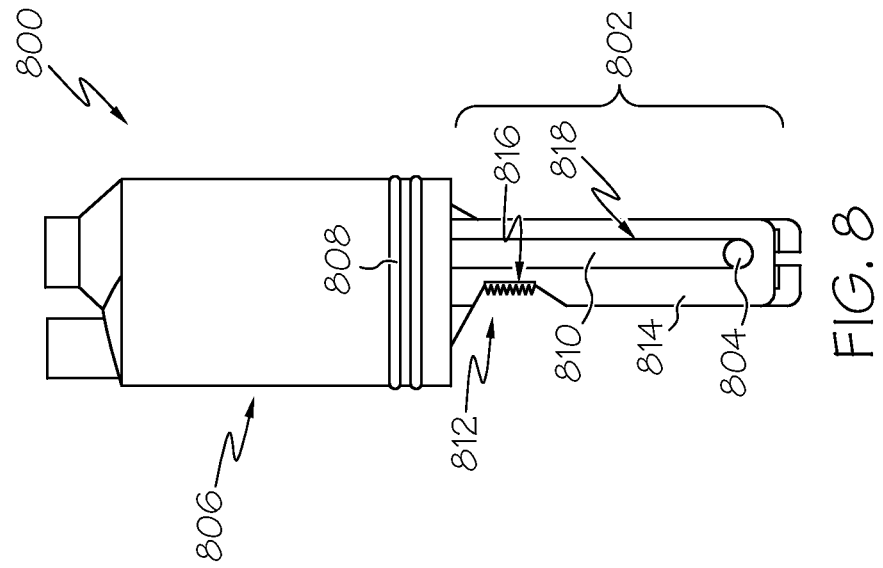
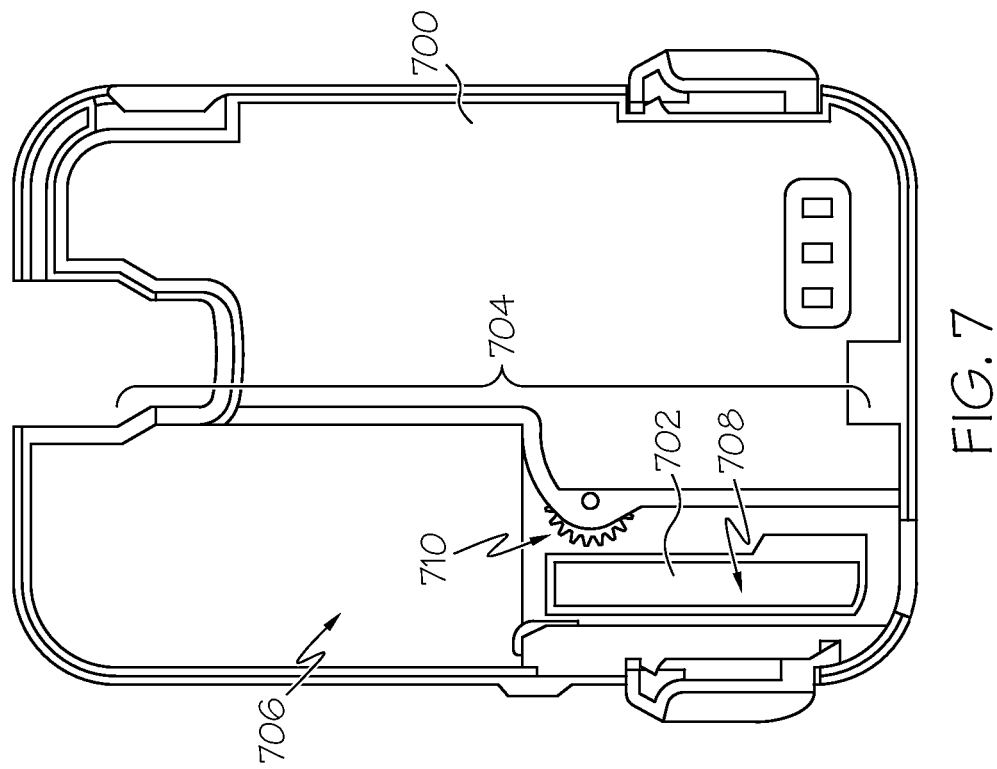

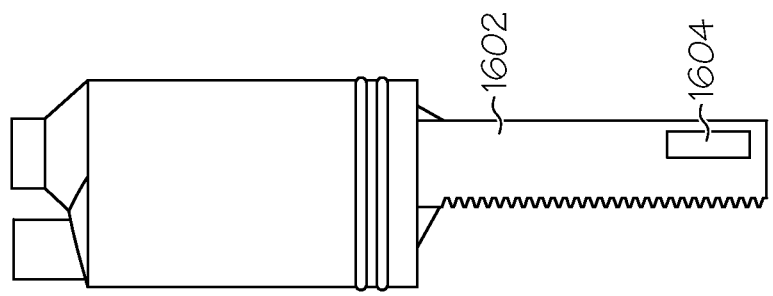
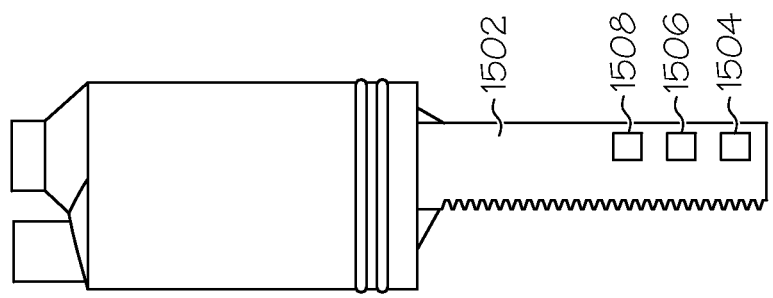

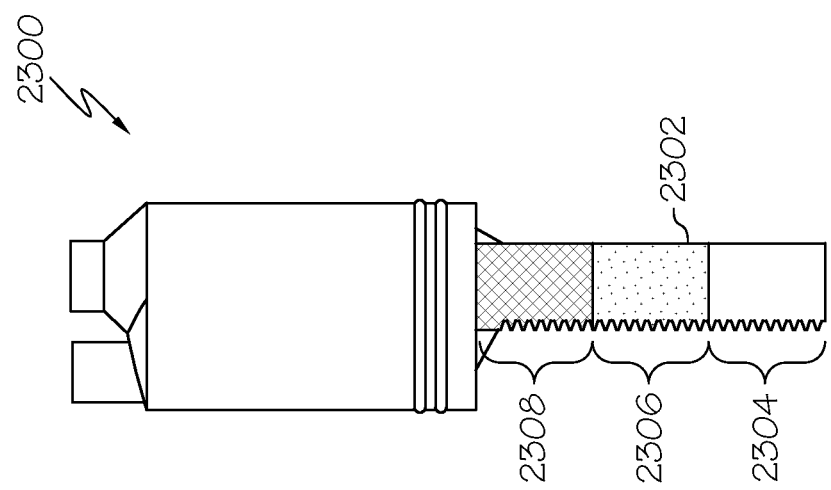

RESERVOIR PLUNGER POSITION MONITORING AND MEDICAL DEVICE INCORPORATING SAME

CROSS-REFERENCE TO RELATED APPLICATIONS

This application is a continuation of U.S. patent application Ser. No. 13/591,129, filed Aug. 21, 2012.

TECHNICAL FIELD

Embodiments of the subject matter described herein relate generally to medical devices, and more particularly, embodiments of the subject matter relate to monitoring the position of a plunger in a fluid infusion device.

BACKGROUND

Infusion pump devices and systems are relatively well-known in the medical devices, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Some fluid infusion devices also include a force sensor designed to detect and indicate a pump malfunction and/or non-delivery of the medication to the patient due to a fluid path occlusion.

In some fluid infusion devices, the reservoir is obscured from the user by being contained inside a housing, thereby preventing the user from being able to visually monitor the amount of fluid remaining in the reservoir. Additionally, the reservoir could become disengaged from the drive system due to an unexpected anomaly within the pump drive system. Thus, it is desirable to inform the user of the remaining amount of fluid in the reservoir and notify the user in the event the reservoir becomes disengaged from the infusion device or there is an anomaly with the drive system.

BRIEF SUMMARY

An embodiment of an infusion device is provided. The infusion device includes a voided portion adapted to receive a shaft portion that includes a shaft coupled to a plunger of a reservoir. The shaft portion includes a detectable feature, and the infusion device includes a sensing arrangement proximate the voided portion to sense the detectable feature.

In another embodiment, an infusion device includes a reservoir having a plunger disposed within a barrel portion, a shaft that is coupled to the plunger and includes a detectable feature, and a sensing arrangement proximate the shaft to sense a position of the detectable feature.

In yet another embodiment, a method of operating an infusion device to deliver fluid from a reservoir is provided. The reservoir includes a plunger coupled to a shaft such that displacement of the shaft results in displacement of the plunger. The infusion device includes a sensing arrangement to sense a detectable feature on the shaft and a motor having a rotor coupled to the shaft to displace the shaft in response to rotation of the rotor and deliver fluid from the reservoir. The method involves operating the motor to displace the shaft and deliver fluid from the reservoir, obtaining a measured shaft position based at least in part on a position of the detectable feature sensed by the sensing arrangement, determining a remaining amount of fluid in the reservoir based on the measured shaft position, and providing a low fluid notification when the determined amount of remaining fluid is less than a threshold value.

In another embodiment, a method for operating an infusion device to deliver fluid from a reservoir involves operating a motor having a rotor coupled to a shaft coupled to a plunger in the reservoir displace the shaft and deliver fluid from the reservoir, obtaining a measured shaft position based at least in part on a position of a detectable feature on the shaft sensed by a sensing arrangement, determining an expected shaft position based on an amount of rotation of the rotor, and identifying an anomalous condition when a difference between the expected shaft position and the measured shaft position exceeds a threshold amount.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 7 is a plan view of an exemplary durable housing including a sensing arrangement that is suitable for use as the durable housing in the fluid infusion device of FIG. 2 in accordance with one embodiment;

FIG. 8 is a plan view of an exemplary fluid reservoir including a detectable feature that is suitable for use with the durable housing of FIG. 7 in the fluid infusion device of FIG. 2 in accordance with one embodiment;

FIG. 15 is a plan view of an exemplary reservoir suitable for use with the durable housing of FIG. 14 in accordance with one embodiment;

FIG. 16 is a plan view of another exemplary reservoir suitable for use with the durable housing of FIG. 14 in accordance with one embodiment;

FIG. 23 is a plan view of another exemplary reservoir suitable for use with the durable housing of FIG. 21 in accordance with one embodiment.

DETAILED DESCRIPTION

Figure 1:
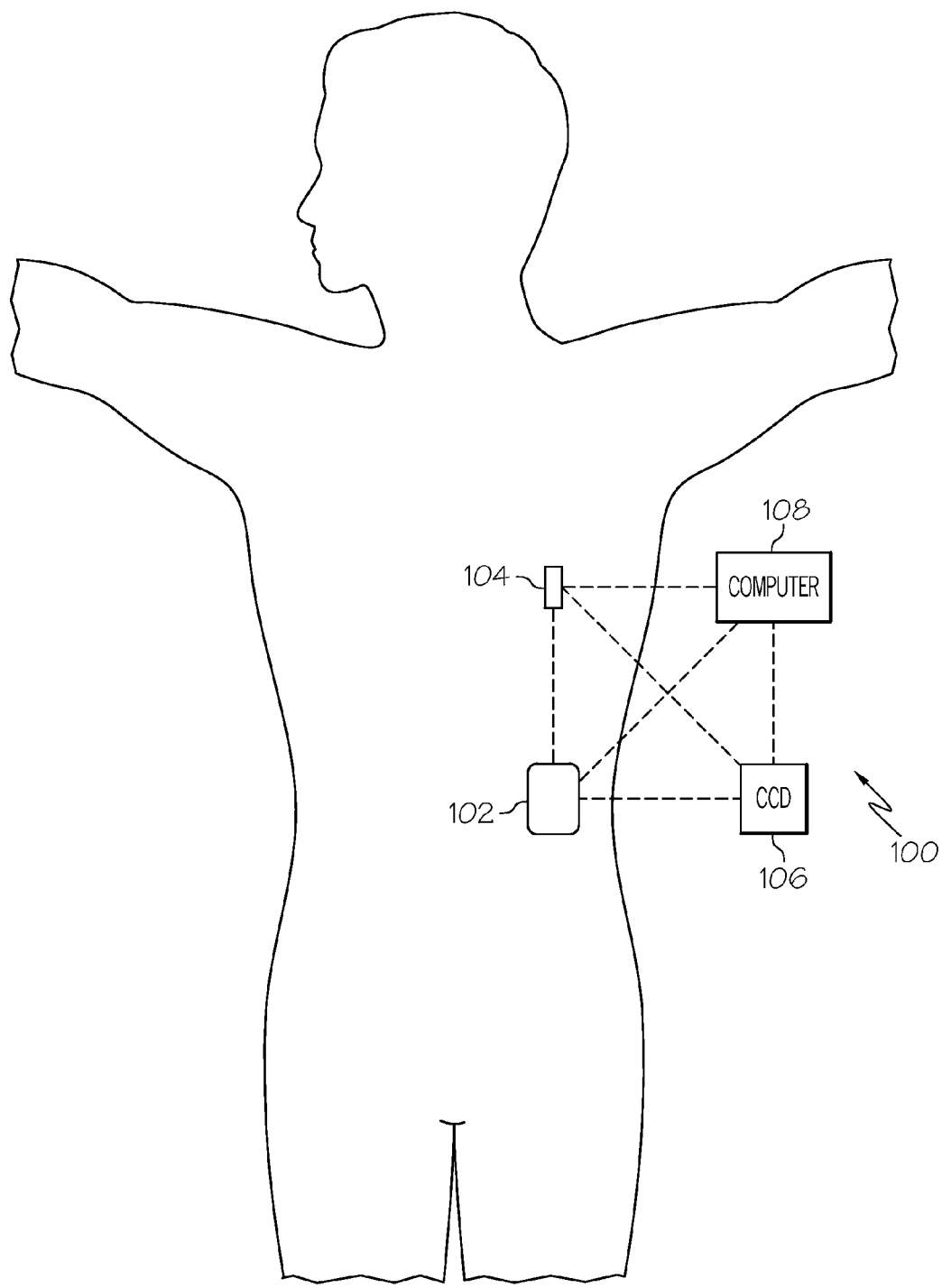
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Embodiments of the subject matter described herein generally relate to infusion devices adapted to sense, measure, or otherwise detect the position of a shaft coupled to a plunger disposed within a barrel of a reservoir to estimate the remaining amount of fluid in the reservoir and identify an anomalous condition based on the shaft position. As described in greater detail below, in exemplary embodiments, the housing of the infusion device includes a voided portion corresponding to the shaft that includes a sensing arrangement capable of sensing or otherwise detecting one or more detectable feature(s) associated with the position of the shaft. In this regard, although the subject matter may be described herein in the context of the detectable feature(s) being provided on the shaft, in other embodiments, the detectable feature(s) may be provided at other locations such that the sensing and/or detection of the detectable feature(s) by the sensing arrangement is influenced by or otherwise corresponds to the position of the shaft. For example, the detectable feature(s) may be provided at a location that allows the shaft to be interposed between the sensing arrangement and the detectable feature(s), such that the position of the shaft influences the ability of the sensing arrangement to sense or otherwise detect the detectable feature(s) and thereby provides an indication of the shaft position.

In exemplary embodiments, based on the measured shaft position obtained using the sensing arrangement, the remaining amount of fluid is estimated to provide the user with indication of the remaining amount of fluid and/or alert the user when the remaining amount falls below a threshold amount where the user would like to be notified to replace and/or refill the reservoir. Additionally, during operation of the infusion device, an expected shaft position may be determined and compared to the measured shaft position for detecting or otherwise identifying an anomalous condition, such as an occlusion condition or a drive system anomaly, when the difference between the expected shaft position and the measured shaft position exceeds a threshold amount. Furthermore, in embodiments where the shaft is integral with or otherwise joined to the plunger of the reservoir, the presence of the reservoir in the infusion device may be detected or otherwise identified based on the measured shaft position. For example, the infusion device may include a housing adapted to receive the reservoir as described below, and seating of the reservoir within the housing may be detected or otherwise identified when the shaft is detected.

While the subject matter described herein can be implemented in any electronic device that includes a displaceable shaft coupled to a motor, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893 which are herein incorporated by reference.

Turning now to FIG. 1, in exemplary embodiments, an infusion system 100 includes, without limitation, a fluid infusion device (or infusion pump) 102, a sensing arrangement 104, a command control device (CCD) 106, and a computer 108. The components of an infusion system may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. patent application Ser. No. 13/049,803, assigned to the assignee of the present application, the subject matter of which is hereby incorporated by reference in its entirety.

In the illustrated embodiment of FIG. 1, the infusion device 102 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like. The sensing arrangement 104 generally represents the components of the infusion system 100 configured to sense a condition of the user, and may include a sensor, a monitor, or the like, for providing data indicative of the condition that is sensed and/or monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108. In various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

As described above, in various embodiments, the CCD 106 and/or the computer 108 include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 may utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, and 7,323,142, all of which are incorporated herein by reference in their entirety. In such embodiments, the sensing arrangement 104 is configured to sense a condition of the user, such as, blood glucose level or the like. The infusion device 102 may be configured to deliver fluid in response to the condition sensed by the sensing arrangement 104. In turn, the sensing arrangement 104 may continue to sense a new condition of the user, allowing the infusion device 102 to deliver fluid continuously in response to the new condition sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
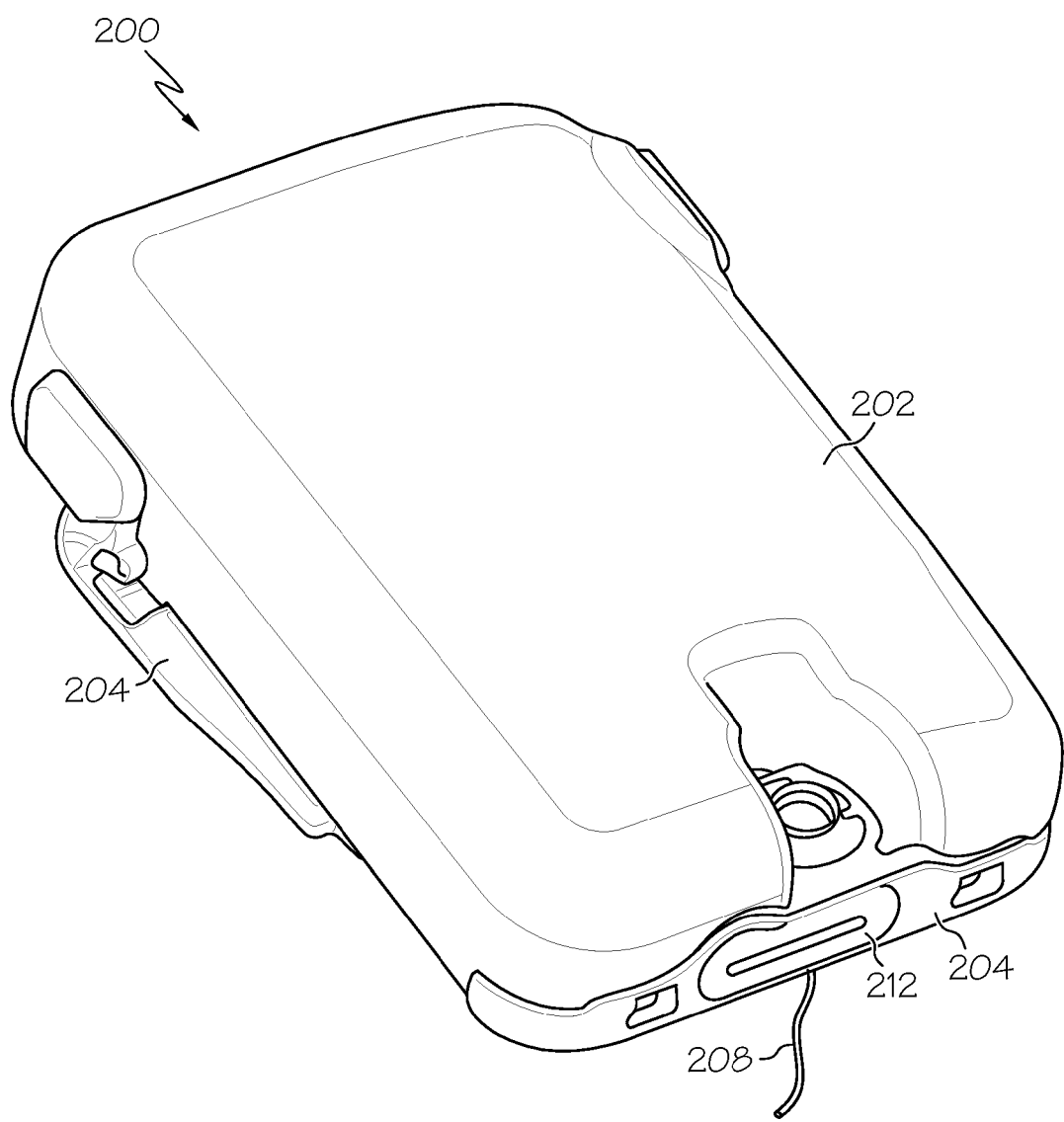
FIG. 2 is a perspective view of an exemplary embodiment of a fluid infusion device suitable for use in the infusion system of FIG. 1.
Figure 3:
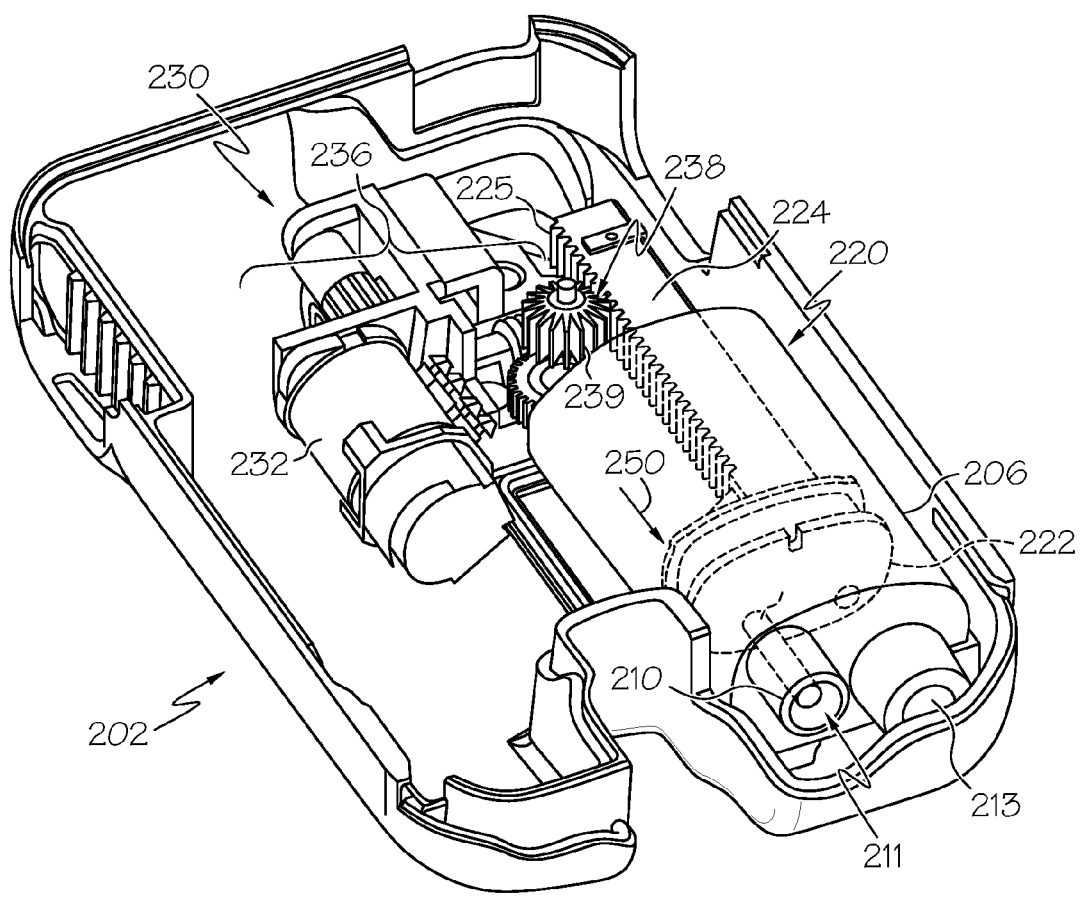
FIG. 3 is a perspective view that depicts internal structure of the durable housing of the fluid infusion device shown in FIG. 2.

FIGS. 2-6 depict an exemplary embodiment of a fluid infusion device 200 suitable for use as the infusion device 102 in the infusion system 100 of FIG. 1. FIGS. 2-3 depict perspective views of the fluid infusion device 200, which includes a durable housing 202 and a base plate 204. While FIG. 2 depicts the durable housing 202 and the base plate 204 as being coupled together, in practice, the durable housing 202 and/or the base plate 204 may include features, structures, or elements to facilitate removable coupling (e.g., pawls, latches, rails, slots, keyways, buttons, or the like) and accommodate a removable/replaceable fluid reservoir 206. As illustrated in FIG. 3, in exemplary embodiments, the fluid reservoir 206 mates with, and is received by, the durable housing 202. In alternate embodiments, the fluid reservoir 206 mates with, and is received by, the base plate 204.

In exemplary embodiments, the base plate 204 is temporarily adhered to the skin of the user, as illustrated in FIG. 1 using, for example, an adhesive layer of material. After the base plate 204 is affixed to the skin of the user, a suitably configured insertion device or apparatus may be used to insert a fluid delivery needle or cannula 208 into the body of the user. The cannula 208 functions as one part of the fluid delivery path associated with the fluid infusion device 200. The durable housing 202 receives the fluid reservoir 206 and retains the fluid reservoir 206 in a substantially fixed position and orientation with respect to the durable housing 202 and the base place 204 while the durable housing 202 and the base plate 204 are coupled. The durable housing 202 is configured to secure to the base plate 204 in a specified orientation to engage the fluid reservoir 206 with a reservoir port receptacle formed in the durable housing 202. In particular embodiments, the fluid infusion device 200 includes certain features to orient, align, and position the durable housing 202 relative to the base plate 204 such that when the two components are coupled together, the fluid reservoir 206 is urged into the reservoir port receptacle to engage a sealing assembly and establish a fluid seal, as described in more detail below.

In exemplary embodiments, the fluid reservoir 206 includes a fluid delivery port 210 that cooperates with the reservoir port receptacle to establish a fluid delivery path. In this regard, the fluid delivery port 210 has an interior 211 defined therein that is shaped, sized, and otherwise configured to receive a sealing element when the fluid reservoir 206 is engaged with the reservoir port receptacle on base plate 204. The sealing element forms part of a sealing assembly for the fluid infusion device 200 and preferably includes one or more sealing elements and/or fluid delivery needles configured to establish fluid communication from the interior of the reservoir 206 to the cannula 208 via the fluid delivery port 210 and a mounting cap 212, and thereby establish a fluid delivery path from the reservoir 206 to the user via the cannula 208. In the illustrated embodiment, the fluid reservoir 206 includes a second fluid port for receiving fluid. For example, the second fluid port 213 may include a pierceable septum, a vented opening, or the like to accommodate filling (or refilling) of the fluid reservoir 206 by the patient, a doctor, a caregiver, or the like.

As illustrated in FIG. 3, the reservoir 206 includes a barrel 220 for containing fluid and a plunger 222 (or stopper) positioned to push fluid from inside the barrel 220 of the reservoir 206 along the fluid path through the cannula 208 to the user. A shaft 224 is mechanically coupled to or otherwise engages the plunger 222, and the shaft 224 has exposed teeth 225 that are configured to mechanically couple or otherwise engage the shaft 224 with a drive system 230 contained in the durable housing 202. In this regard, the shaft 224 functions as a rack gear as part of a rack and pinion gear configuration, as described in greater detail below. Although the subject matter may be described herein in the context of the shaft 224 being integral with or otherwise part of the plunger 222, in practice, the shaft 224 and the plunger 222 may be provided separately.

Figure 4:
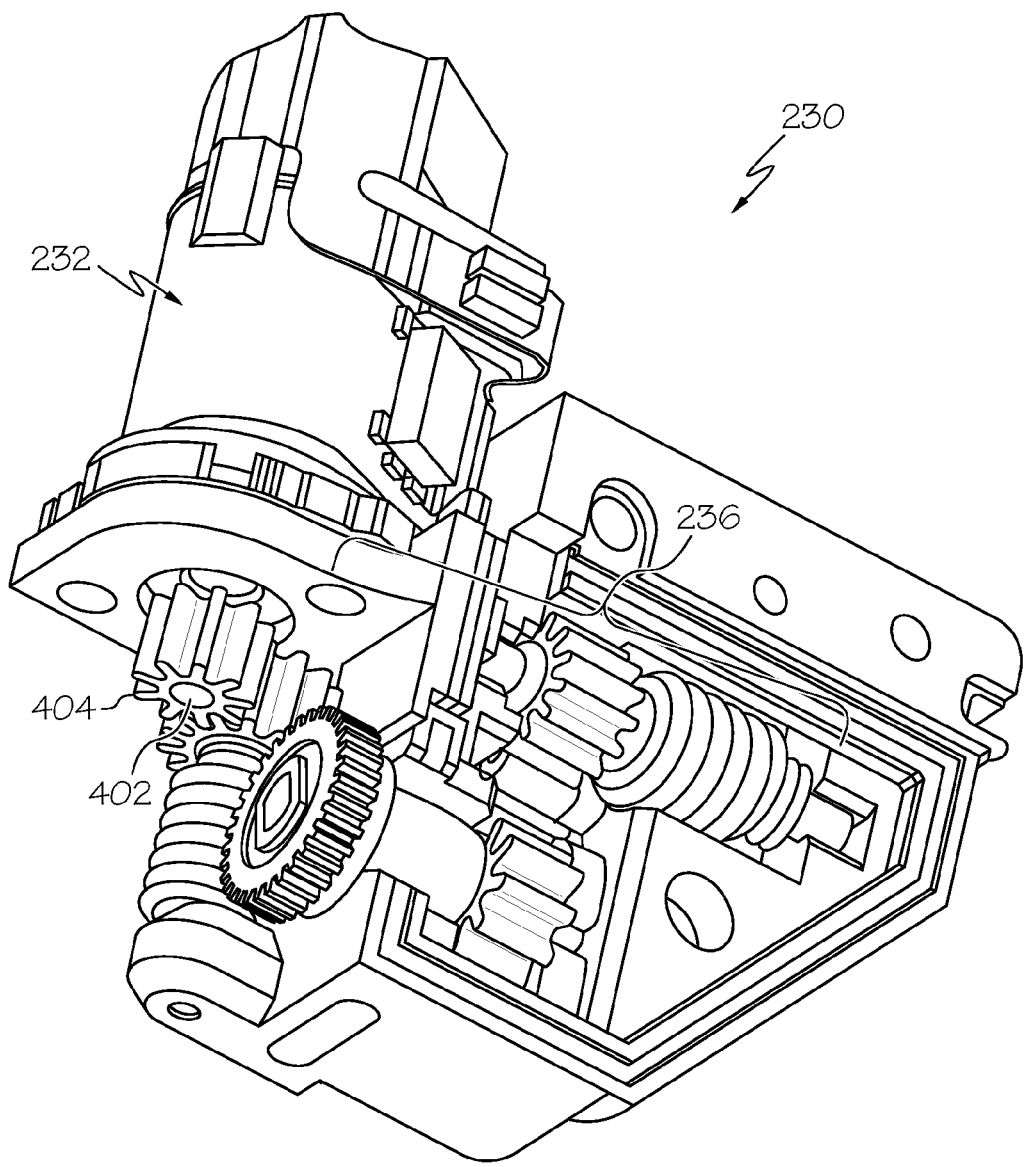
FIG. 4 is a perspective view of the drive system in the durable housing of the fluid infusion device of FIGS. 2-3.
Figure 5:
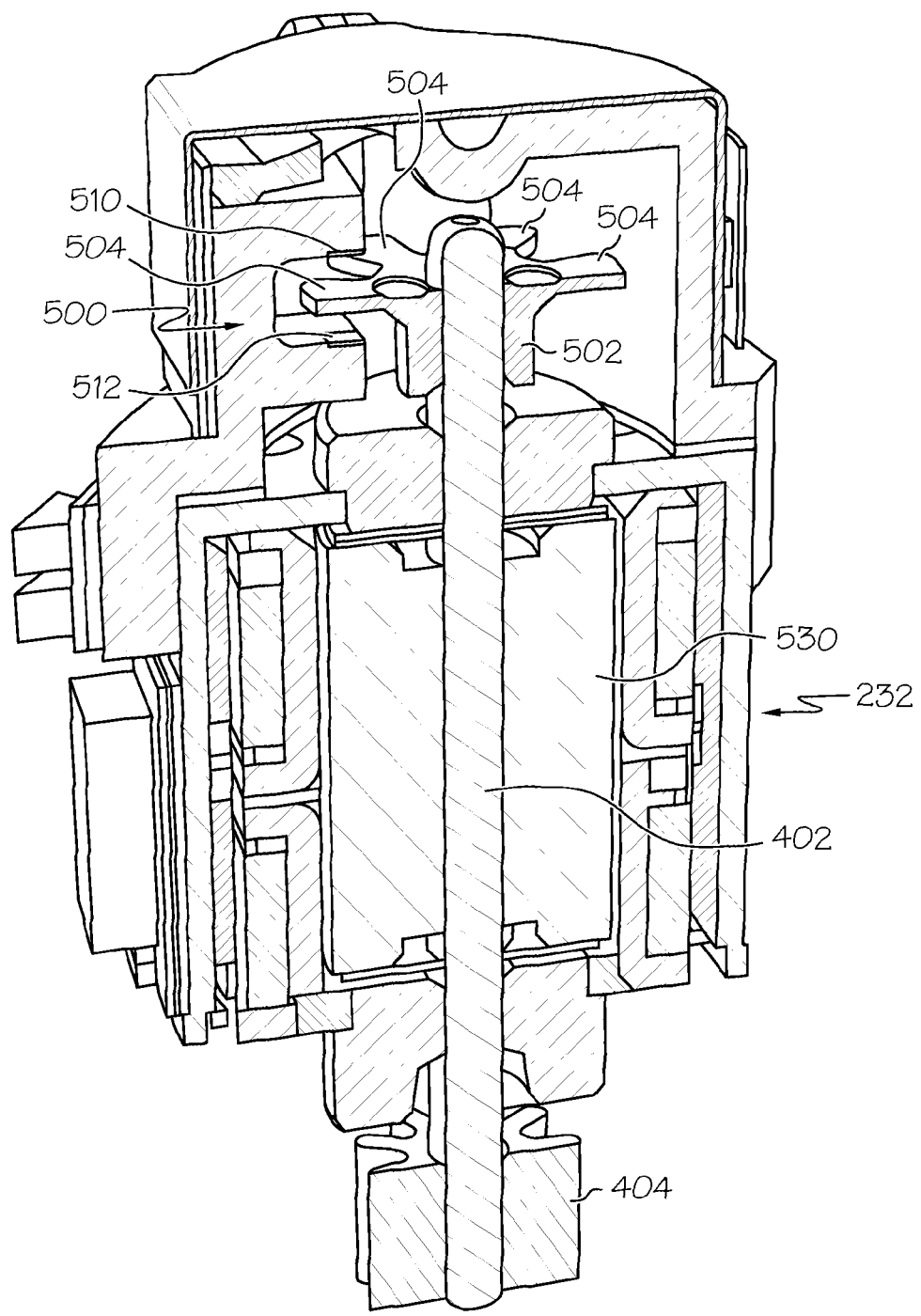
FIG. 5 is cross-sectional perspective view of the motor of drive system of FIG. 4 illustrating a sensor integrated therein.
Figure 6:
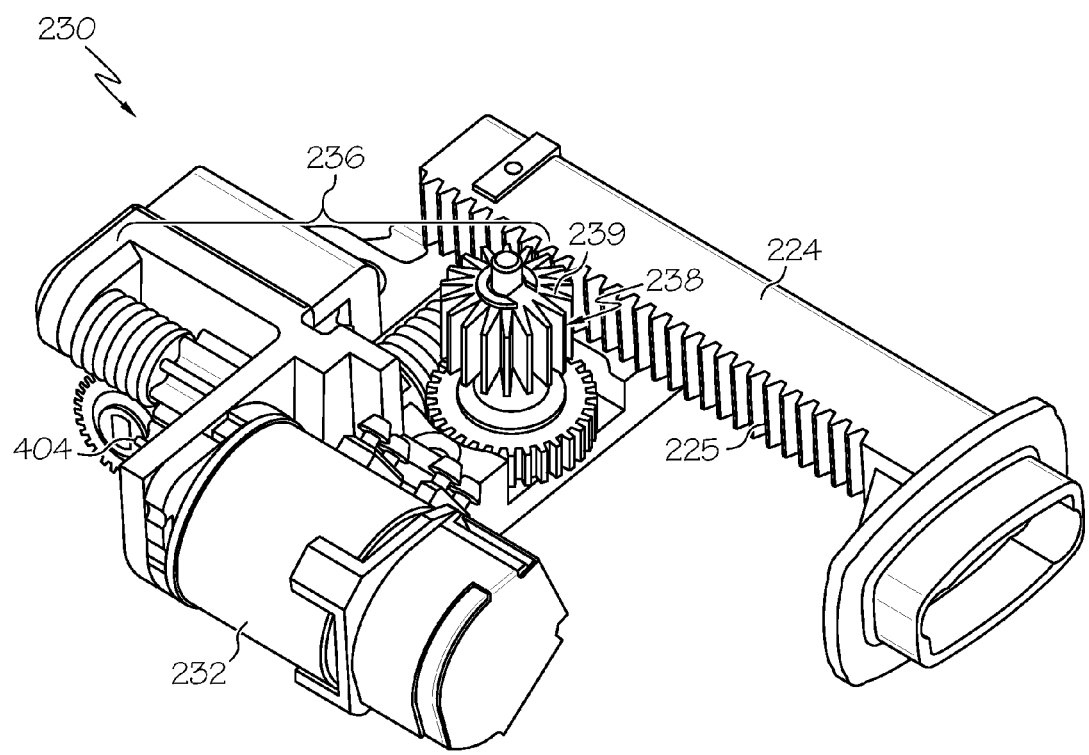
FIG. 6 is a perspective view illustrating the drive system engaged with the shaft of the plunger when the fluid reservoir is seated within the durable housing of FIG. 3.

FIGS. 4-6 depict perspective and cross-sectional views of the drive system 230 provided in the durable housing 202. Various aspects of the motor drive system 230 may be similar to those described in U.S. patent application Ser. No. 13/049,803. The drive system 230 includes a motor 232 having a rotor 530 that is mechanically coupled to a gear assembly 236 that translates rotation of the rotor 530 of the motor 232 to translational displacement the plunger 222 in the direction 250 of the fluid delivery port 210. In exemplary embodiments, the motor 232 is realized as a DC motor, such as a stepper motor or brushless DC motor capable of precisely controlling the amount of displacement of the plunger 222 during operation of the infusion device 200, as described in greater detail below. As best illustrated in FIGS. 4-5, in exemplary embodiments, the rotor 530 of the motor 232 is mechanically coupled to a rotary shaft 402, which, in turn, is mechanically coupled to a first gear 404 of the gear assembly 236. In the illustrated embodiment of FIGS. 4-5, the first gear 404 is coaxial and/or concentric to and disposed about the rotary shaft 402, and the first gear 404 is affixed to or otherwise integrated with the rotary shaft 402 such that the first gear 404 and the rotary shaft 402 rotate in unison. The gear assembly 236 also includes a second gear 238 (or pinion gear) having exposed teeth 239 that are configured to mate with or otherwise engage the exposed teeth 225 on the shaft 224, such that rotation or displacement of the pinion gear 238 produces a corresponding linear displacement of the shaft 224 in direction 250, which results in a corresponding displacement of the plunger 222 in direction 250 to deliver fluid from the user. The gear assembly 236 includes various additional gears and potentially other drive train components (e.g., screws, cams, ratchets, jacks, pulleys, pawls, clamps, nuts, slides, bearings, levers, beams, stoppers, plungers, sliders, brackets, guides, bearings, supports, bellows, caps, diaphragms, bags, heaters, and the like) configured to mechanically couple the first gear 404 to the pinion gear 238 so that rotation (or displacement) of the first gear 404 produces a corresponding rotation (or displacement) of the pinion gear 238.

During operation of the fluid infusion device 200, when the motor 232 is operated to rotate the rotor 530, the rotary shaft 402 rotates in unison with the rotor 530 to cause a corresponding rotation of the first gear 404, which, in turn, actuates the gears of the gear assembly 236 to produce a corresponding rotation or displacement of the pinion gear 238, which, in turn, displaces the shaft 224 in direction 250. In this manner, the rotary shaft 402 translates rotation (or displacement) of the rotor 530 into a corresponding rotation (or displacement) of the gear assembly 236 such that the exposed teeth 239 of the pinion gear 238 to apply force to the exposed teeth 225 of the shaft 224 of the plunger 222 in the direction 250 of the fluid delivery port 210 to thereby displace the plunger 222 in the direction 250 of the fluid delivery port 210 and dispense, expel, or otherwise deliver fluid from the barrel 220 of the reservoir 206 to the user via the fluid delivery path provided by the cannula 208.

Referring to FIG. 5, in an exemplary embodiment, a sensor 500 is configured to measure, sense, or otherwise detect rotation (or displacement) of the rotary shaft 402 and/or the rotor 530 of the motor 232. For convenience, but without limitation, the motor position sensor 500 may alternatively be referred to herein as a motor position sensor or rotor position sensor. In exemplary embodiments, the rotary shaft 402 includes a detectable feature that is measurable or otherwise detectable by the motor position sensor 500. In the illustrated embodiment, a rotary member (or wheel) 502 is provided on the rotary shaft 402 and includes a plurality of protruding features (or arms) 504 that are measurable or otherwise detectable by the motor position sensor 500. In the illustrated embodiment, the wheel 502 is coaxial and/or concentric to and disposed about the rotary shaft 402, and the wheel 502 is affixed to or otherwise integrated with the rotary shaft 402 such that the wheel 502 and the rotary shaft 402 rotate in unison. In this manner, rotation (or displacement) of the wheel 502 corresponds to the displacement of the rotary shaft 402 and/or the rotor 530 of the motor 232.

In exemplary embodiments, the sensor 500 is realized as an incremental position sensor configured to measure, sense, or otherwise detect incremental rotations of the rotary shaft 402 and/or the rotor 530 of the motor 232. For example, in accordance with one or more embodiments, the sensor 500 is realized as a rotary encoder. In alternative embodiments, the sensor 500 may be realized using any other suitable sensor, such as (but not limited to) a magnetic sensor, optical sensor (or other light detector), tactile sensor, capacitive sensor, inductive sensor, and/or the like. In exemplary embodiments, the incremental position sensor 500 may be configured to count or otherwise sense incremental rotations of the motor 232 via the wheel 502, for example, by counting each time a protruding feature 504 passes by the sensor 500. In this regard, when the number of protruding features 504 equals or otherwise corresponds to the number of discrete motor steps of the stepper motor 232, the incremental position sensor 500 counts or otherwise senses the number of motor steps traversed by the rotary shaft 402 and/or rotor of the motor 232. In some embodiments, the sensor 500 includes an emitter 510 and a detector 512 disposed on opposite sides of the wheel 502 such that at least a portion of the protruding features 504 passes between the emitter 510 and the detector 512 as the wheel 502 rotates. In this regard, the sensor 500 may detect or otherwise count each instance when a protruding feature 504 interrupts a transmission from the emitter 510 to the detector 512. Alternatively, the sensor 500 may detect or otherwise count each instance a transmission from the emitter 510 to the detector 512 is uninterrupted or otherwise completed (e.g., via gaps between protruding features 504).

Still referring to FIGS. 2-6, as described in greater detail below in the context of FIGS. 7-12, in exemplary embodiments, to allow the position of the plunger 222 and/or shaft 224 to be monitored, measured, or otherwise detected, the shaft 224 includes one or more detectable features provided or otherwise formed thereon and a voided portion of the durable housing 202 that corresponds to or otherwise surrounds the shaft 224 includes a sensing arrangement capable of sensing or otherwise detecting the one or more detectable features on the shaft 224. In this regard, when the reservoir 206 is inserted in the durable housing 202, the sensing arrangement is disposed proximate the shaft 224 to sense or otherwise detect the one or more detectable features on the shaft 224. In exemplary embodiments, the sensing arrangement provides an electrical output signal that is indicative of or otherwise corresponds to the position or location of the detectable feature(s), which in turn, corresponds to the position or location of the shaft 224 relative to the durable housing 202, which, in turn, corresponds to the position or location of the plunger 222 within the barrel 220 of the reservoir 206. For example, in one or more embodiments, the detectable feature influences an electrical characteristic (e.g., a resistance, capacitance, inductance, or the like) of the sensing arrangement based on the position of the detectable feature with respect to the sensing arrangement. In this manner, an electrical output signal from the sensing arrangement is influenced by the detectable features on the shaft 224 and is thereby indicative of the position or location of the shaft 224. Additionally, when the shaft 224 is integral with the plunger 222 or another feature of the reservoir 206, the electrical output signal from the sensing arrangement that is influenced by the detectable features on the shaft 224 is also indicative of the reservoir 206 being seated within the housing 202 and/or device 200. In one or more alternative embodiments, the detectable feature(s) may be optically detected, for example, using a photodiode or the like, that is provided in the durable housing 202. In yet other embodiments, the detectable feature(s) may have a magnetic field or another electromagnetic characteristic that is detected or otherwise sensed by corresponding sensors provided in the durable housing 202 (e.g., Hall effect sensors, capacitive sensors, inductive sensors, and the like). It should be noted that there are numerous potential sensing techniques and/or configurations that may be utilized to sense, measure, or otherwise detect the position of the shaft 224 relative to the durable housing 202, and the exemplary sensing configurations described herein are provided for purposes of explanation and are not intended to be exhaustive or limiting. In this regard, the subject matter described herein is not limited to a particular sensing technique described herein.

FIG. 7 illustrates an exemplary embodiment of a durable housing 700 including a sensing arrangement 702 that may be utilized as the durable housing 202 in the fluid infusion device 200 of FIG. 2, and FIG. 8 illustrates an exemplary embodiment of a reservoir 800 that includes a shaft portion 802 having a feature 804 that is detectable by the sensing arrangement 702 in the housing 700. The durable housing 700 and the reservoir 800 are similar to the durable housing 202 and the fluid reservoir 206 described above in the context of FIGS. 2-6, and the common features and/or functionality of the durable housing 700 and the reservoir 800 will not be redundantly described in detail in the context of FIGS. 7-8. As described above, the reservoir 800 includes a barrel 806 having a plunger 808 (or stopper) disposed therein that is mechanically coupled to a shaft 810 having exposed teeth 812 configured to engage the exposed teeth of a pinion gear 710 in the housing 700.

In the illustrated embodiment of FIG. 8, the reservoir 800 includes a guide portion 814 encompassing the shaft 810 that includes a first cutout portion 816 to expose at least some of the teeth 812 of the shaft 810 and a second cutout portion 818 to expose or otherwise accommodate the detectable feature 804. As illustrated in FIG. 7, the housing 700 includes a voided region 704 (or cavity) adapted to receive the reservoir 800 that includes a first portion 706 that corresponds to the barrel 806 of the reservoir 800 and a second portion 708 that corresponds to the shaft portion 802 of the reservoir 800. The pinion gear 710 is positioned within the housing 700 such that the exposed teeth of the pinion gear 710 extend into the voided shaft portion 708 to engage the teeth 812 of the reservoir 800 when the reservoir 800 is inserted in the voided region 704. In an exemplary embodiment, the sensing arrangement 702 is formed in (or on) a wall of the voided shaft portion 708 so that the sensing arrangement 702 is proximate to (or adjacent to) the shaft portion 802 of the reservoir 800 when the reservoir 800 is inserted in the voided region 704.

In accordance with one or more exemplary embodiments, the detectable feature 804 is provided on the side of the shaft 810 that faces the sensing arrangement 702 at or near the distal end of the shaft 810, that is, the end of shaft 810 distal to the plunger 808 and/or barrel 806. In this manner, when the shaft 810 and/or plunger 808 is fully retracted (e.g., when the reservoir 800 is full of fluid), the detectable feature 804 is at or near the distal end of the sensing arrangement 702. Thus, as the shaft 810 and/or plunger 808 is displaced to deliver fluid from the reservoir, the detectable feature 804 approaches the end of the sensing arrangement 702 proximate the barrel 806 and produces a corresponding change in the electrical output signal generated by the sensing arrangement 702. In this manner, the position of the detectable feature 804 relative to the sensing arrangement 702 functions as a proxy for the position of the plunger 808 with respect to the barrel 806, thereby allowing the amount of fluid remaining in the reservoir 800 to be estimated based at least in part on the sensed position of the detectable feature 804.

As described in greater detail below in the context of FIGS. 9-10, in accordance with one embodiment, the sensing arrangement 702 is realized as a resistive sensing arrangement having a variable resistance that is influenced by a location (or position) of the detectable feature 804 with respect to the sensing arrangement. For example, the resistive sensing arrangement may include one or more layers of material that, when compressed, provide a resistance corresponding to the location (or position) on the sensing arrangement 702 where the one or more layers are compressed. In this regard, the detectable feature 804 may be realized as a protruding feature, such as a peg or pin, that extends from the shaft 810 through the cutout portion 818 to contact the sensing arrangement 702 and compress the one or more layers to produce a resistance corresponding to the position of the protruding feature with respect to the sensing arrangement 702. In this regard, as the shaft 810 is displaced in response to rotation of the pinion gear 710, the location (or position) of the protruding feature changes by a corresponding amount to compress the layers of the sensing arrangement 702 at a different location to produce a corresponding change in the resistance of the sensing arrangement 702.

In accordance with another embodiment, the sensing arrangement 702 is realized as a capacitive sensing arrangement having a variable capacitance corresponding to a location (or position) of the detectable feature 804 with respect to the sensing arrangement 702. In this regard, the detectable feature 804 may be realized as a conductive material, such as a metal material, that provides a capacitance or a change in capacitance between the detectable feature 804 and the sensing arrangement 702. In this regard, as the shaft 810 is displaced in response to rotation of the pinion gear 710, the location (or position) of the detectable feature 804 changes by a corresponding amount to vary the capacitance of the capacitive sensing arrangement in a manner that corresponds to the location of the detectable feature 804 with respect to the sensing arrangement 702. In alternative embodiments, the sensing arrangement 702 may be realized as an inductive sensing arrangement having a variable inductance corresponding to a location (or position) of the detectable feature 804 with respect to the sensing arrangement 702.

Figure 9:
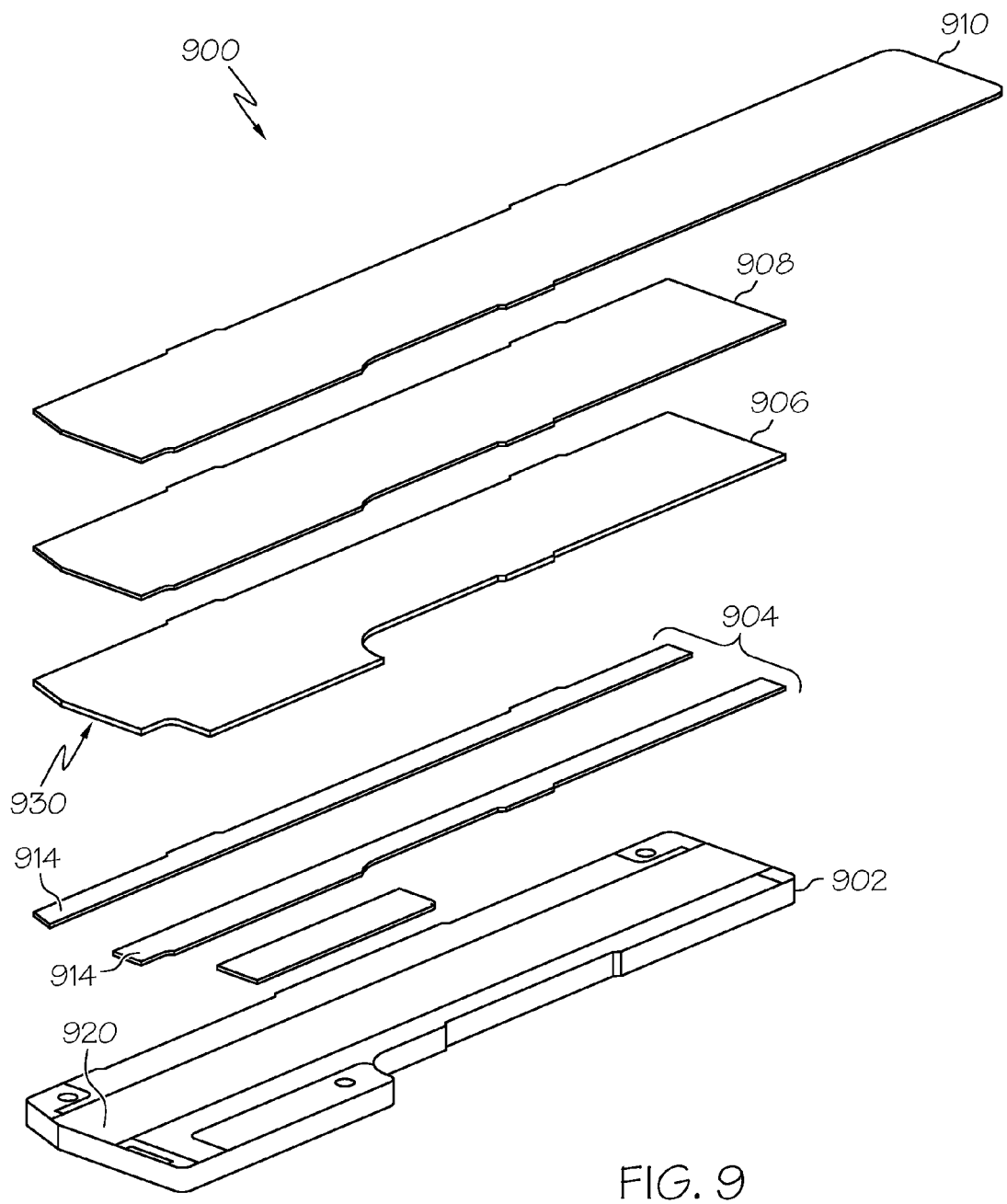
FIG. 9 is an exploded perspective view of an exemplary resistive sensing arrangement suitable for use as the sensing arrangement in the durable housing of FIG. 7 in accordance with one embodiment.
Figure 10:
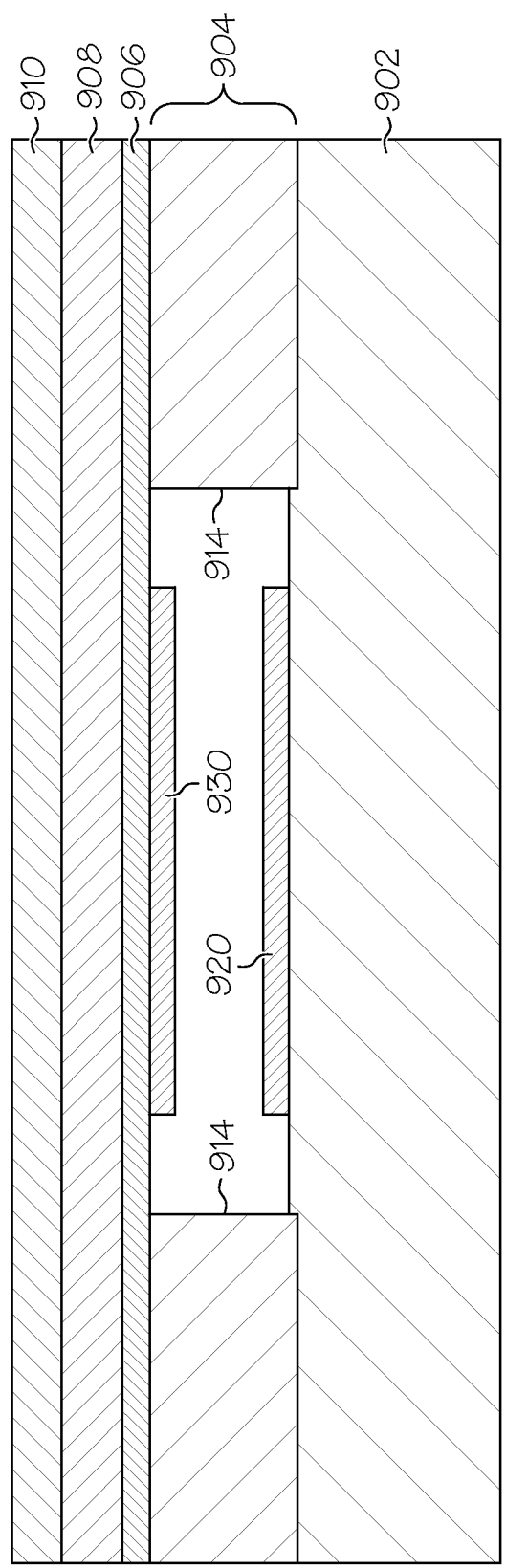
FIG. 10 is a cross-sectional view of the resistive sensing arrangement of FIG. 9.

FIGS. 9-10 depict an exemplary embodiment of a resistive sensing arrangement 900 suitable for use as the sensing arrangement 702 in the durable housing 700 of FIG. 7. The sensing arrangement 900 includes, without limitation, a bottom conductive layer 902, a spacer layer 904, an upper conductive layer 906, and an adhesive layer 908. A flexible cover layer 910 is provided overlying the layers 902, 904, 906, 908 to seal the layers 902, 904, 906, 908 within the housing 700 and protect the sensing arrangement 900 from environmental elements that could interfere with its operation. In exemplary embodiments, the cover layer 910 is realized as a thin layer of flexible yet resilient material (which may or may not be the same material as the remainder of the housing 700) that is capable of being flexed without permanent deformation, such as a polycarbonate polybutylene terephthalate (PC/PBT) blend material, that, in turn, is affixed to, joined to, or otherwise integral with the surrounding surfaces of the housing 700 that define the voided shaft portion 708 to seal the remaining layers 902, 904, 906, 908 within the housing 700. In this regard, the cover layer 910 may be understood as being part of the housing 700. The bottom conductive layer 902 is realized as a substantially rigid material having a conductive resistive carbon ink layer 920 deposited or otherwise formed thereon. In accordance with one embodiment, the bottom conductive layer 902 is realized as a layer of FR-4 printed circuit board (PCB) material. The upper conductive layer 906 is realized as a flexible material having another conductive resistive carbon ink layer 930 deposited or otherwise formed on the bottom surface that corresponds to or is otherwise aligned with the resistive carbon ink layer 920 on the upper surface of the bottom conductive layer 902. The spacer layer 904 is realized as two longitudinal portions 914 of a rigid material that are affixed to the upper surface of the bottom conductive layer 902 and the bottom surface of the upper conductive layer 906 along the edges of the conductive layers 902, 906 such that conductive layers 902, 906 are spaced apart from one another in the absence of a compressive force applied to the upper surface of the upper conductive layer 906. The adhesive layer 908 is affixed to the upper surface of the upper conductive layer 906 and the bottom surface of the cover layer 910 so that the underlying layers 902, 904, 906 of the sensing arrangement 900 are affixed to the cover layer 910.

Referring now to FIGS. 7-10, in an exemplary embodiment, the cover layer 910 is integrated with or otherwise provided on a wall of the voided shaft portion 708 that faces the detectable feature 804 on the shaft 810. In this regard, the resistive carbon ink layers 920, 930 are positioned on the conductive layers 902, 906 such that they are substantially aligned with the detectable feature 804. When the sensing arrangement 702 is realized as the sensing arrangement 900, the detectable feature 804 is realized as a protruding feature that contacts the cover layer 910 when the reservoir 800 is provided within the voided region 704 of the housing 700. The protruding feature 804 on the shaft 810 compresses the cover layer 910 and the upper conductive layer 906 and causes the resistive carbon ink layers 920, 930 to contact one another at the location where the protruding feature 804 contacts the sensing arrangement 900. In this regard, the contact between the resistive carbon ink layers 920, 930 provides a resistive electrical connection between the conductive layers 902, 906. In an exemplary embodiment, the bottom resistive carbon ink layer 920 is configured as a voltage divider, wherein the magnitude of the voltage across the resistive carbon ink layer 920 is influenced by the resistance of the resistive carbon ink layer 920 between an end of the sensing arrangement 900 and the location where the protruding feature 804 contacts the sensing arrangement 900, which corresponds to the length of the resistive carbon ink layer 920 between the end of the sensing arrangement 900 and the location where the protruding feature 804 contacts the sensing arrangement 900. In this manner, as the protruding feature 804 moves closer to and/or further from the end of the sensing arrangement 900, the voltage across the resistive carbon ink layer 920 and/or the sensing arrangement 900 increases and/or decreases by a corresponding amount, and is thereby indicative of the position of the shaft 810 with respect to the sensing arrangement 702, 900 and/or the housing 700.

Figure 11:
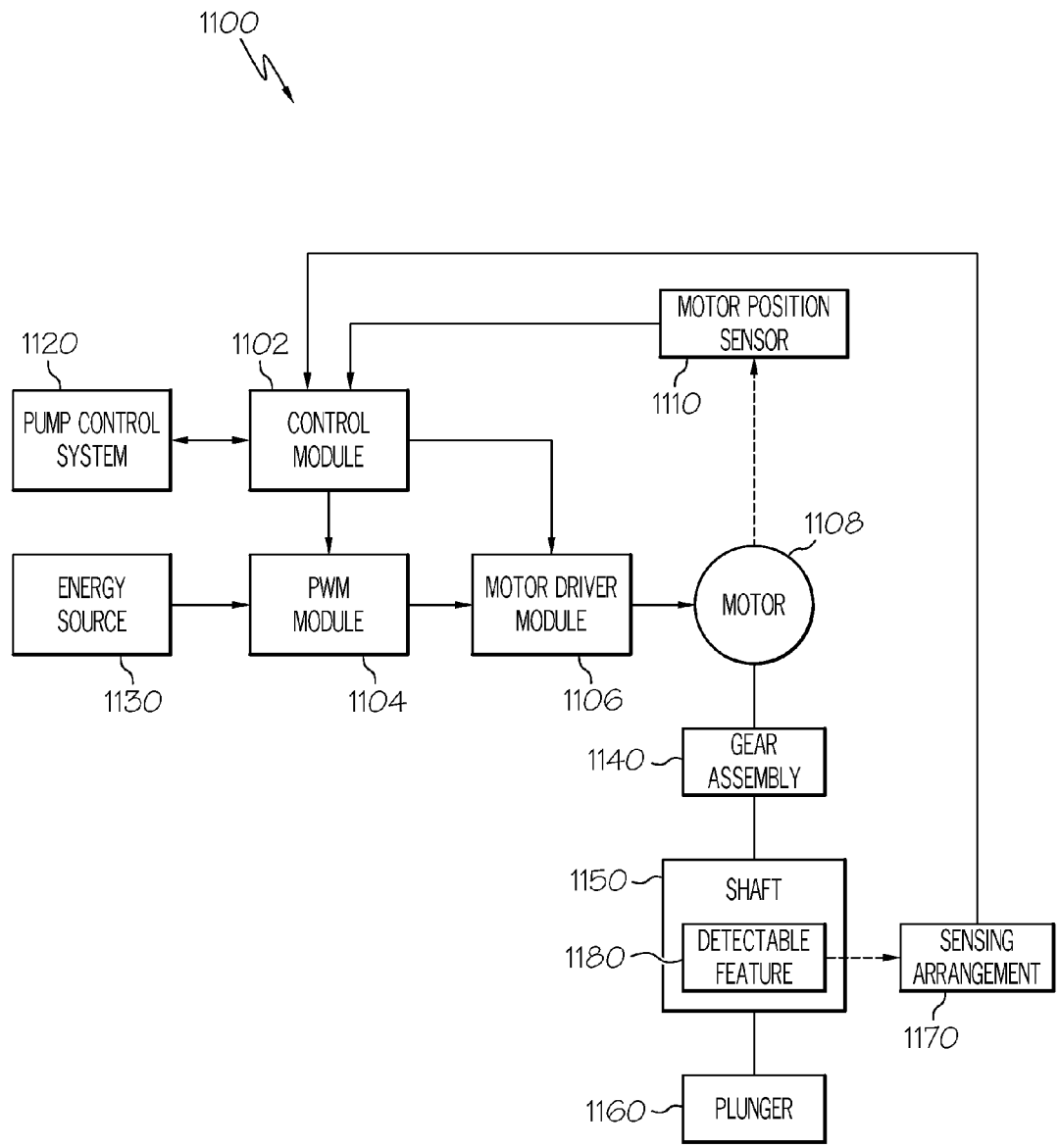
FIG. 11 is a block diagram of an exemplary control system suitable for use with a fluid infusion device.

FIG. 11 depicts an exemplary embodiment of a control system 1100 suitable for use with an infusion device in an infusion system, such as infusion device 200 or infusion device 102 in the infusion system 100. The illustrated control system 1100 includes, without limitation, a control module 1102, a pulse-width modulation (PWM) module 1104, a motor driver module 1106, a motor 1108 (e.g., motor 232), and a motor (or rotor) position sensor 1110 (e.g., sensor 500). In exemplary embodiments, the control system 1100 is suitably configured to operate the motor 1108 to displace a plunger 1160 and provide a desired amount of fluid to a user in response to a dosage command indicative of the desired amount of fluid to be delivered that is received from a pump control system 1120, as described in greater detail below. In this regard, the pump control system 1120 generally represents the electronics and other components of the infusion system that process sensor data (e.g., from sensing arrangement 104) pertaining to a condition of the user and control operation of the fluid infusion device according to a desired infusion delivery program in a manner that is influenced by sensor data measured by and/or received from the sensing arrangement 104 or otherwise dictated by the user. In practice, the features and/or functionality of the pump control system 1120 may be implemented by control electronics located in the fluid infusion device 102, 200, the CCD 106 and/or the computer 108. It should be understood that FIG. 11 is a simplified representation of the system 1100 for purposes of explanation and is not intended to limit the subject matter described herein in any way. For example, in practice, the features and/or functionality of the control module 1102 may implemented by or otherwise integrated into the pump control system 1120, or vice versa.

In the illustrated embodiment, the PWM module 1104 generally represents the combination of circuitry, hardware and/or other electrical components configured to generate a pulse-width modulated voltage output applied to the motor 1108 via the motor driver module 1106. In an exemplary embodiment, the PWM module 1104 is coupled to an energy source 1130, such as a battery housed within the infusion device 200 (e.g., in the housing 202), to receive a supply voltage. Based on a duty cycle setting for the PWM module 1104, the PWM module 1104 generates or otherwise produces a pulse-width modulated voltage output that oscillates between the supply voltage provided by the energy source 1130 and a ground (or reference) voltage over a time interval (e.g., the PWM period), wherein the pulse-width modulated voltage output is equal to the supply voltage for a percentage of the time interval corresponding to the duty cycle setting. For example, if the supply voltage provided by the energy source 1130 is equal to five volts and the duty cycle setting is equal to 30%, then the pulse-width modulated voltage output generated by the PWM module 1104 may be a square wave having a magnitude equal to five volts for 30% of the time interval and zero volts for the remaining 70% of the time interval. In this regard, the duty cycle setting corresponds to the width of a portion of the square wave (e.g., the portion corresponding the supply voltage), and accordingly, the duty cycle setting may alternatively be referred to herein as the PWM width setting. As described in greater detail below, in exemplary embodiments, the control module 1102 is coupled to the PWM module 1104 to adjust, modify, or otherwise control the duty cycle setting of the PWM module 1104.

In an exemplary embodiment, the motor 1108 is a stepper motor or brushless DC motor having a toothed rotor and a number of sets of windings, wherein the number of teeth on the rotor along with the number of winding sets and the physical arrangement of the winding sets with respect to the rotor teeth provides a finite number of motor steps within a revolution of the rotor. In this regard, as used herein, a "motor step" or any variant thereof should be understood as referring to an incremental rotation of the rotor of the motor 1108 that is dictated by the number of teeth of the rotor along with the number and/or arrangement of the winding sets. As described above in the context of FIGS. 2-6, in an exemplary infusion pump embodiment, the rotor of the motor 1108 is mechanically coupled to the plunger 1160 via a gear assembly 1140 (e.g., gear assembly 236) and a shaft 1150 (e.g., shaft 224 or shaft 810). In this regard, the gear assembly 236 includes gears and/or other drive train components configured to translate rotation of the rotor of the motor 1108 into a corresponding amount of displacement of the shaft 1150, which in turn, displaces the plunger 1160 (e.g., plunger 222 or plunger 808) into the barrel (e.g., barrel 206 or barrel 806) of a reservoir (e.g., reservoir 206 or reservoir 800) to deliver fluid (e.g., insulin) to the body of a user.

The control system 1100 also includes one or more detectable features 1180 associated with the shaft 1150 and a sensing arrangement 1170 capable of sensing, measuring, or otherwise detecting the relative position of the detectable feature(s) 1180. As described above in the context of FIG. 8, in accordance with one or more embodiments, the detectable feature(s) 1180 are formed on or otherwise integrated into the shaft 1150, however, in other embodiments, the detectable feature(s) 1180 may be separate from the shaft. For example, as described in greater detail below in the context of FIG. 13, one or more detectable feature(s) may be provided inside the guide portion 814 so that a portion of the shaft 810 may be interposed between the detectable feature(s) and the sensing arrangement 702 to influence the ability of the sensing arrangement 702 to sense, measure, or otherwise detect by detectable feature(s) in a manner that corresponds to the amount of the shaft 810 that is interposed between the detectable feature(s) and the sensing arrangement 702. The control module 1102 is coupled to the sensing arrangement 1170 utilizes the position of the detectable feature(s) 1180 sensed by the sensing arrangement 1170 to obtain a measured position of the shaft 1150 and utilizes the measured shaft position to determine the amount of fluid remaining in the reservoir and/or identify anomalous conditions, as described in greater detail below in the context of FIG. 12.

Still referring to FIG. 11, the motor driver module 1106 generally represents the combination of circuitry, hardware and/or other electrical components configured to sequentially apply a voltage provided at a supply voltage input of the motor driver module 1106 to one or more sets of windings of the motor 1108 in a particular order to produce a corresponding number of commanded motor steps of rotation by the motor 1108. In the illustrated embodiment, the supply voltage input of the motor driver module 1106 is coupled to the output of the PWM module 1104, such that the motor driver module 1106 provides the pulse-width modulated voltage from the PWM module 1104 to the one or more sets of windings of the motor 1108 in a particular order under control of the control module 1102. In this regard, in some embodiments, the motor driver module 1106 is coupled to the control module 1102 to receive a commanded number of motor steps from the control module 1102, wherein in response to the commanded number of motor steps, the motor driver module 1106 sequentially applies the pulse-width modulated voltage from the PWM module 1104 to the sets of windings of the motor 1108 in the appropriate order to produce the commanded number of motor steps. In other embodiments, the control module 1102 may operate the switches and/or other circuitry of the motor driver module 1106 to produce the commanded number of motor steps. The frequency at which the motor driver module 1106 is operated (e.g., the frequency at which the pulse-width modulated voltage is changed from being applied to one winding set to another winding set) is less than the frequency of the pulse-width modulated voltage output from the PWM module 1104, such that the pulse-width modulated voltage output oscillates between the supply voltage and the ground voltage multiple times over the time period (e.g., the inverse of the motor driver frequency) during which the pulse-width modulated voltage output is applied to a particular set of windings of the motor 1108.

In an exemplary embodiment, the motor position sensor 1110 is realized as an incremental position sensor, such as a rotary encoder, that is configured to sense, measure, or otherwise detect an incremental rotation of the rotor of the motor 1108, in a similar manner as described above in the context of the sensor 500 of FIG. 5. In exemplary embodiments, the resolution of the position sensor 1110 is greater than or equal to the resolution of the motor 1108, that is, the number of discrete incremental rotations measurable by the position sensor 1110 over one revolution of the rotor of the motor 1108 (e.g., the number of detectable features 504) is greater than or equal to the number of discrete motor steps over one revolution of the rotor of the motor 1108. In accordance with one or more embodiments, the output of the position sensor 1110 is coupled to the control module 1102 to provide dynamic closed-loop PWM control of the motor 1108, as described in greater detail below.

Still referring to FIG. 11, the control module 1102 generally represents the hardware, software, firmware and/or combination thereof that is configured to receive or otherwise obtain a commanded dosage from the pump control system 1120, convert the commanded dosage to a commanded number of motor steps, and command, signal, or otherwise operate the motor driver module 1106 to cause the motor 1108 to produce the commanded number of motor steps. As described in greater detail below in the context of FIG. 12, in exemplary embodiments, the control module 1102 obtains or otherwise determines the measured position of the shaft 1150 via the sensing arrangement 1170 and estimates or otherwise determines an amount of fluid remaining in a fluid reservoir based on the corresponding position of the plunger 1160. Additionally, the control module 1102 determines an expected position of the shaft based on the commanded number of motor steps and/or the commanded dosage, and determines whether an occlusion condition or some other anomalous condition exists when a difference between the expected position of the shaft and the measured position exceeds a threshold amount. Depending on the embodiment, the control module 1102 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. Furthermore, the steps of a method or algorithm described in connection with the embodiments disclosed herein may be embodied directly in hardware, in firmware, in a software module executed by the control module 1102, or in any practical combination thereof. In exemplary embodiments, the control module 1102 includes or otherwise accesses a memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the control module 1102. The computer-executable programming instructions, when read and executed by the control module 1102, cause the control module 1102 to perform the tasks, operations, functions, and processes described in greater detail below.

Figure 12:
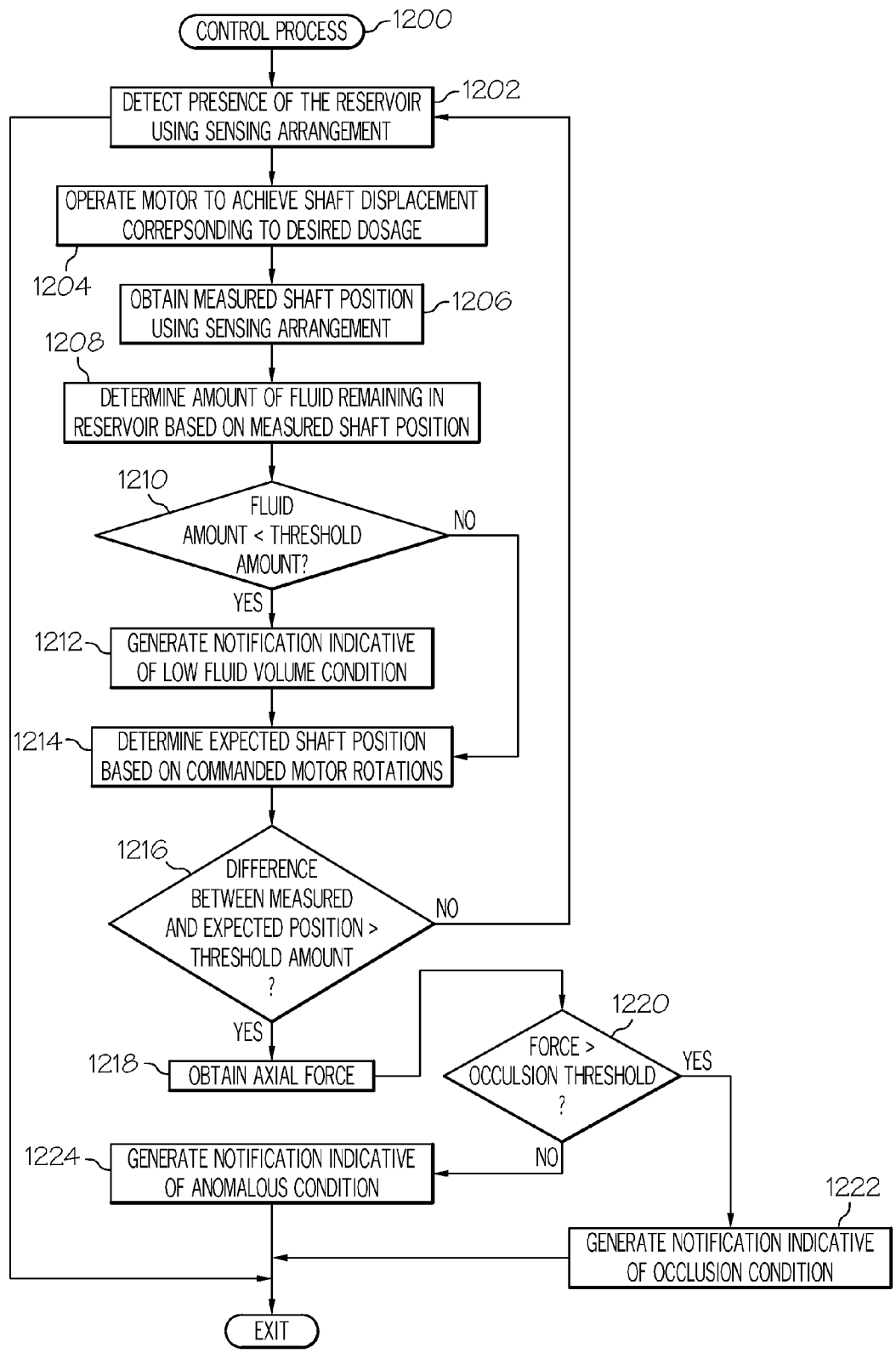
FIG. 12 is a flow diagram of an exemplary control process suitable for use with the control system of FIG. 11.

FIG. 12 depicts an exemplary control process 1200 suitable for implementation by the control system 1100 to monitor the position of the shaft 1150 and/or plunger 1160 while operating an infusion device to deliver fluid to a user. The various tasks performed in connection with the control process 1200 may be performed by software, hardware, firmware, or any combination thereof. For illustrative purposes, the following description refers to elements mentioned above in connection with FIG. 11. In practice, portions of the control process 1200 may be performed by different elements of the control system 1100, such as, for example, the control module 1102, the PWM module 1104, the motor driver module 1106, the motor 1108, the position sensor 1110, the detectable feature(s) 1180 and/or the sensing arrangement 1170. It should be appreciated that the control process 1200 may include any number of additional or alternative tasks, the tasks need not be performed in the illustrated order and/or the tasks may be performed concurrently, and/or the control process 1200 may be incorporated into a more comprehensive procedure or process having additional functionality not described in detail herein. Moreover, one or more of the tasks shown and described in the context of FIG. 12 could be omitted from a practical embodiment of the control process 1200 as long as the intended overall functionality remains intact.

In accordance with one or more embodiments, the control process 1200 begins by detecting or otherwise identifying the presence of a reservoir in the infusion device using the sensing arrangement (task 1202). For example, as described above in the context of FIGS. 7-10, in accordance with one or more embodiments, when the reservoir 800 is provided within the voided region 704 of the housing 700 and the housing 700 is coupled to a base plate (e.g., base plate 204), the sensing arrangement 702, 900 is capable of sensing or otherwise detecting the presence of the detectable feature 804 in contact with or otherwise proximate to the sensing arrangement 702, 900. In this regard, the control module 1102 monitors or otherwise obtains the electrical output signal from the sensing arrangement 1170 to determine whether the presence of a detectable feature 1180 has been detected. In accordance with one embodiment, the control module 1102 detects or otherwise identifies seating of the reservoir by obtaining the electrical output signal from the sensing arrangement 1170 and determining the reservoir is seated within the housing of the infusion device when the electrical output signal is indicative of the detectable feature 1180 contacting the housing of the infusion device or otherwise being within a threshold distance of the sensing arrangement 1170. For example, when the sensing arrangement 1170 generates an electrical output signal in response to physical contact with the detectable feature 1180 on the shaft 1150 (e.g., resistive sensing arrangement 900), the control module 1102 detects seating of the reservoir when the sensing arrangement 1170 generates an electrical output signal indicating presence of the detectable feature 1180. In other embodiments, when the sensing arrangement 1170 generates an electrical output signal based on the proximity of the detectable feature 1180 on the shaft 1150, the control module 1102 may detect seating of the reservoir when the sensing arrangement 1170 generates an electrical output signal indicating that the detectable feature 1180 of the shaft 1150 is within a threshold distance of the sensing arrangement 1170 that indicates the reservoir is seated. In accordance with one or more embodiments, in response to detecting the initial seating of the reservoir, the control module 1102 automatically initiates a priming sequence or the like to initialize the positioning of the plunger 1160 within the reservoir for subsequent operation.

In an exemplary embodiment, after the presence of the reservoir is detected, the control process 1200 continues by operating the motor to achieve a displacement of the plunger corresponding to a desired dosage of fluid to be administered to a user (task 1204). In this regard, the control module 1102 obtains commands from the pump control system 1120 corresponding to the desired dosage and operates the motor 1108 to rotate the rotor by an amount that produces an amount of displacement of the shaft 1150 and/or plunger 1160 that corresponds to the desired dosage. For example, the pump control system 1120 may determine or otherwise receive (e.g., from the CCD 106 and/or the computer 108) a dose (or bolus) of fluid to be provided to the user based on a sensed condition of the user (e.g., a blood glucose level). In some embodiments, the pump control system 1120 converts the amount of fluid to be provided to the user into a commanded displacement of the plunger 1160, converts the commanded displacement of the plunger 1160 to a corresponding number of motor steps (or incremental rotations) based on the relationship between one motor step of rotation and the resulting linear displacement of the shaft 1150 and/or plunger 1160, and provides that commanded number of motor steps to the control module 1102. In other embodiments, the pump control system 1120 provides the amount of fluid to be provided to the user to the control module 1102, wherein the control module 1102 converts the commanded dosage into a corresponding number of commanded motor steps based on the amount of displacement of the plunger 1160 corresponding to that amount of fluid.

In accordance with one or more embodiments, the control module 1102 utilizes closed-loop dynamic PWM control by dynamically adjusting the duty cycle setting of the PWM module 1104 to ensure the rotor rotates by the commanded amount. For example, the control module 1102 may determine an expected number of incremental rotations of the rotor of the motor 1108 that should be measured by the position sensor 1110 based on the commanded number of motor steps corresponding to the commanded dosage. After operating the motor driver module 1106 to produce the commanded number of motor steps of rotation, the control module 1102 obtains a measured number of incremental rotations of the rotor of the motor 1108 from the position sensor 1110, and based on differences between the measured number and the expected number of incremental rotations, increases or otherwise adjusts the PWM width setting of the PWM module 1104 to achieve the commanded number of motor steps during subsequent operation of the motor 1108.

After operating the motor to achieve a desired displacement of the plunger, the control process 1200 continues by obtaining a measured position of the shaft using the sensing arrangement and estimating or otherwise determining the amount of fluid remaining in the fluid reservoir based on the measured position of the shaft (tasks 1206, 1208). In this regard, when the detectable feature(s) 1180 are provided on the plunger 1160, the control module 1102 obtains, from the sensing arrangement 1170, electrical signals indicative of the position of the detectable feature(s) 1180 with respect to the sensing arrangement 1170 and/or the durable housing. For example, when the sensing arrangement 1170 is realized as the resistive sensing arrangement 900, the control module 1102 may obtain a voltage across the sensing arrangement 900 (which is influenced by the resistance of the sensing arrangement 900, which, in turn, is influenced by the position of the detectable feature 804 on the shaft 810) and determine the position of the shaft relative to the sensing arrangement 900 based on that obtained voltage relative to a reference voltage or the voltage(s) across the sensing arrangement 900 when the detectable feature is located at the end(s) of the sensing arrangement 900. Based on the measured position of the shaft relative to the sensing arrangement 1170 and/or the durable housing, the control module 1102 may determine or otherwise estimate the corresponding position of the plunger 1160 within the barrel of the reservoir, and based on the position of the plunger 1160 within the barrel of the reservoir, determine or otherwise estimate the amount of fluid remaining in the reservoir. For example, a calibration procedure may be performed to compress the resistive carbon ink layers 920, 930 into contact at specific locations associated with the shaft position for known amounts of fluid remaining in the reservoir to correlate the resulting electrical output signals generated by the resistive sensing arrangement 900 to the respective remaining amounts of fluid. The relationship between the electrical output signals and the remaining amounts of fluid (or contact locations) may be interpolated and/or extrapolated (e.g., by performing linear regression or another suitable regression technique) to characterize the electrical output signal generated by the resistive sensing arrangement 900 as a function of the remaining amount of fluid in the reservoir (or a particular location where the resistive carbon ink layers 920, 930 are in contact). In this manner, a calibration table may be created that correlates values for remaining amounts of fluid in the reservoir and/or shaft positions to values of the electrical output signal generated by the resistive sensing arrangement 900 over the potential range of displacement for the shaft. Thus, the control module 1102 may utilize the calibration table to correlate the electrical output signal obtained from the sensing arrangement 1170 to an estimated amount of fluid remaining in the reservoir. In accordance with one or more embodiments, the control module 1102 may provide the estimated amount of fluid remaining in the reservoir to the pump control system 1120 for display or presentation to the user (e.g., via CCD 106 and/or computer 108).

As described in greater detail below in the context of FIG. 13, in some embodiments, the control module 1102 may augment the measured position of the shaft 1150 obtained using the sensing arrangement 1170 with a number of incremental rotor rotations measured by the position sensor 1110 to improve the resolution of the estimated amount of fluid. For example, if the detectable feature(s) 1180 and/or the sensing arrangement 1170 are configured to provide discrete measurements of the shaft position (e.g., as opposed to the continuous measurement range provided by sensing arrangement 900), the control module 1102 may utilize incremental rotations measured by the position sensor 1110 to estimate or otherwise determine the measured position of the plunger 1160 when the shaft position is between two discrete measurement positions. In this regard, the sensing arrangement 1170 may be comprised of a plurality of sensing elements, wherein the control module 1102 utilizes incremental rotations measured by the position sensor 1110 to estimate or otherwise determine the measured position of the plunger 1160 when the shaft position is between or overlaps two sensing elements. For example, the control module 1102 may implement a counter that counts the incremental rotations detected by the position sensor 1110 and is reset each time the detectable feature 1180 changes between discrete positions measurable by the sensing arrangement 1170 (e.g., each time the detectable feature 1180 passes from one sensing element to another). The value of the counter may be used to determine the position of the shaft 1150 and/or plunger 1160 based on the position of the detectable feature 1180 relative to the next discrete position, that is, the amount by which the detectable feature 1180 is offset from a current and/or previous discrete position. For example, the control module 1102 may convert the value of the counter into an offset amount of displacement based on the relationship between an incremental rotation of the rotor and a corresponding linear displacement of the shaft 1150

(e.g., the displacement of the shaft 1150 that would result from an incremental rotation of the rotor), and add or subtract the offset amount from the position of the detectable feature 1180 measured by the sensing arrangement 1170.

Still referring to FIG. 12, in an exemplary embodiment, the control process 1200 continues by determining whether the estimated amount of remaining fluid is less than a threshold amount of fluid indicative of a low fluid volume condition in the reservoir and generating or otherwise providing a notification when the estimated amount of remaining fluid is less than the threshold amount (tasks 1210, 1212). In this regard, the threshold amount of fluid may be configured or otherwise chosen by a user of the fluid infusion device 102, 200 (e.g., using the CCD 106 and/or the computer 108) to correspond to a level of fluid in the reservoir where the user would like to be reminded or otherwise notified to refill or replace the reservoir. In some embodiments, the control module 1102 provides a notification of the low fluid volume condition to the pump control system 1120 or another supervisory system or module (e.g., the CCD 106 and/or the computer 108) in response to determining the estimated amount of fluid remaining is less than the threshold amount. For example, the control module 1102 may generate an interrupt signal that is handled by the pump control system 1120. In response to the notification from the control module 1102, the pump control system 1120 may generate an auditory and/or visual alert to the user, for example, by causing the CCD 106 and/or the computer 108 to generate one or more auditory cues (e.g., a beep) or display one or more visual cues to notify the user of the low fluid volume condition.

In an exemplary embodiment, the control process 1200 continues by determining an expected position of the shaft and/or plunger based on the commanded rotation of the motor and determining whether a difference between the expected position of the shaft and/or plunger and the measured position of the shaft and/or plunger obtained using the sensing arrangement is greater than a threshold amount (tasks 1214, 1216). In this regard, the threshold amount is indicative of a difference between the measured shaft position and the expected shaft position that indicates that the drive system and/or motor 1108 is not displacing the shaft and/or plunger in the desired manner due to an anomalous condition, such as a fluid path occlusion or a drive system anomaly (e.g., a stripped or slipped gear). The control module 1102 may determine the expected position of the plunger 1160 by obtaining an initial position of the shaft (e.g., via the sensing arrangement 1170) prior to operating the motor 1108 to produce a commanded rotation, converting the commanded rotation to a corresponding displacement of the plunger 1160 based on the relationship between the motor steps (or incremental rotations) for the motor 1108 and the linear displacement of the shaft 1150, and add or subtract that resulting displacement to the initial shaft position to obtain the expected shaft position after the motor 1108 has been operated to produce the commanded rotation. In other embodiments, the control module 1102 may convert the number of incremental rotations measured by the position sensor 1110 to an expected displacement of the shaft 1150 based on the relationship between an incremental rotation detected by the position sensor 1110 and the corresponding linear displacement of the shaft 1150, and add or subtract that expected displacement to the initial position. In an exemplary embodiment, when the difference between the expected position of the shaft and/or plunger and the measured position of the shaft and/or plunger is less than the threshold amount, the control process 1200 repeats the loop defined by tasks 1202, 1204, 1206, 1208, 1210, 1212, 1214 and 1216 throughout operation of the fluid infusion device to deliver fluid to the user and notify the user when the reservoir should be replaced and/or refilled. In this regard, in accordance with one or more embodiments, whenever the control process 1200 fails to detect presence of the reservoir, the control process 1200 generates or otherwise provides a notification indicative of an anomalous condition within the fluid infusion device (e.g., task 1224). For example, the control module 1102 may indicate that the reservoir has become unseated to the pump control system 1120, which, in turn provides a notification to the user (e.g., by generating an auditory and/or visual alert) so that the user may reseat the reservoir.

Still referring to FIG. 12, in an exemplary embodiment, when the difference between the expected position of the shaft and/or plunger and the measured position of the shaft and/or plunger is greater than the threshold amount, the control process 1200 continues by obtaining an axial force aligned with the shaft and/or plunger and determining whether the axial force exceeds a threshold force value indicative of a fluid path occlusion (tasks 1218, 1220). For example, the fluid infusion device may include a force sensor configured to measure axial forces applied by the shaft 1150 and/or plunger 1160 in a direction aligned with the longitudinal axis of the shaft 1150 (e.g., direction 250). In this regard, the force sensor may be positioned within the durable housing (e.g., within the gear assembly 236) such that the force sensor is subjected to a reactionary compressive force when the drive system and/or motor is operated to displace the shaft 1150 and/or plunger 1160 in the axial direction in opposition to the fluid pressure in the reservoir. Thus, if an occlusion develops within the fluid path that blocks fluid delivery from the fluid infusion device to the body of the user, the fluid pressure increases as the shaft 1150 and/or plunger 1160 is forced forward in the axial direction by the motor 1108, which, in turn, increases the force applied to the force sensor. However, if an anomalous condition exists within the drive system and/or fluid infusion device that decouples the shaft 1150 and/or plunger 1160 from the motor 1108, such as a stripped or slipped gear or another drive system anomaly, rotation of the rotor of the motor 1108 displaces the shaft 1150 and/or plunger 1160 by a reduced amount (if at all) and the force sensor will not be subjected to rapidly increasing forces as the motor 1108 is operated as compared to an occlusion condition. Accordingly, when the axial force measured by the force sensor is greater than the threshold force value indicative of a fluid path occlusion and the difference between the expected shaft position and measured shaft position exceeds the threshold amount, the control process 1200 detects or otherwise identifies an occlusion condition and generates or otherwise provides a notification indicative of the occlusion condition (task 1222). Conversely, when the difference between the expected shaft position and measured shaft position exceeds the threshold amount but the axial force measured by the force sensor is less than the occlusion threshold force value, the control process 1200 detects or otherwise identifies a drive system anomaly or some other anomalous condition (e.g., a stripped gear) in the infusion device and generates or otherwise provides a notification indicative of the anomalous condition within the fluid infusion device (task 1224).

In accordance with one or more embodiments, the control module 1102 is coupled to the force sensor and provides a notification of an anomalous condition in the drive system to the pump control system 1120 or another supervisory system or module (e.g., the CCD 106 and/or the computer 108)

when the axial force measured by the force sensor is less than the threshold force indicative of a fluid path occlusion and the difference between the expected position and the measured position of the shaft and/or plunger is greater than a threshold amount. In response, the pump control system 1120 may generate an auditory and/or visual alert to the user to notify the user of the anomalous condition. Conversely, the control module 1102 may provide a notification of an occlusion condition to the pump control system 1120 when the axial force measured by the force sensor is greater than the threshold force and the difference between the expected position and the measured position of the shaft and/or plunger is greater than the threshold amount, wherein the pump control system 1120 generates an auditory and/or visual alert to the user to notify the user of the occlusion condition in response to the notification from the control module 1102. In other embodiments, the control module 1102 generates or otherwise provides a notification to the pump control system 1120 when the difference between the expected position and the measured position of the shaft and/or plunger exceeds the threshold amount, wherein the pump control system 1120 is coupled to the force sensor and determines whether the difference between the expected position and the measured position of the shaft and/or plunger is attributable to a fluid path occlusion or another anomalous condition, such as a drive system anomaly. In this manner, the difference between the expected position and the measured position of the shaft and/or plunger may be used to monitor the health of the drive system while also verifying, confirming, or otherwise augmenting occlusion detection algorithms and/or techniques performed by the pump control system 1120 and/or the fluid infusion device.

Figure 13:
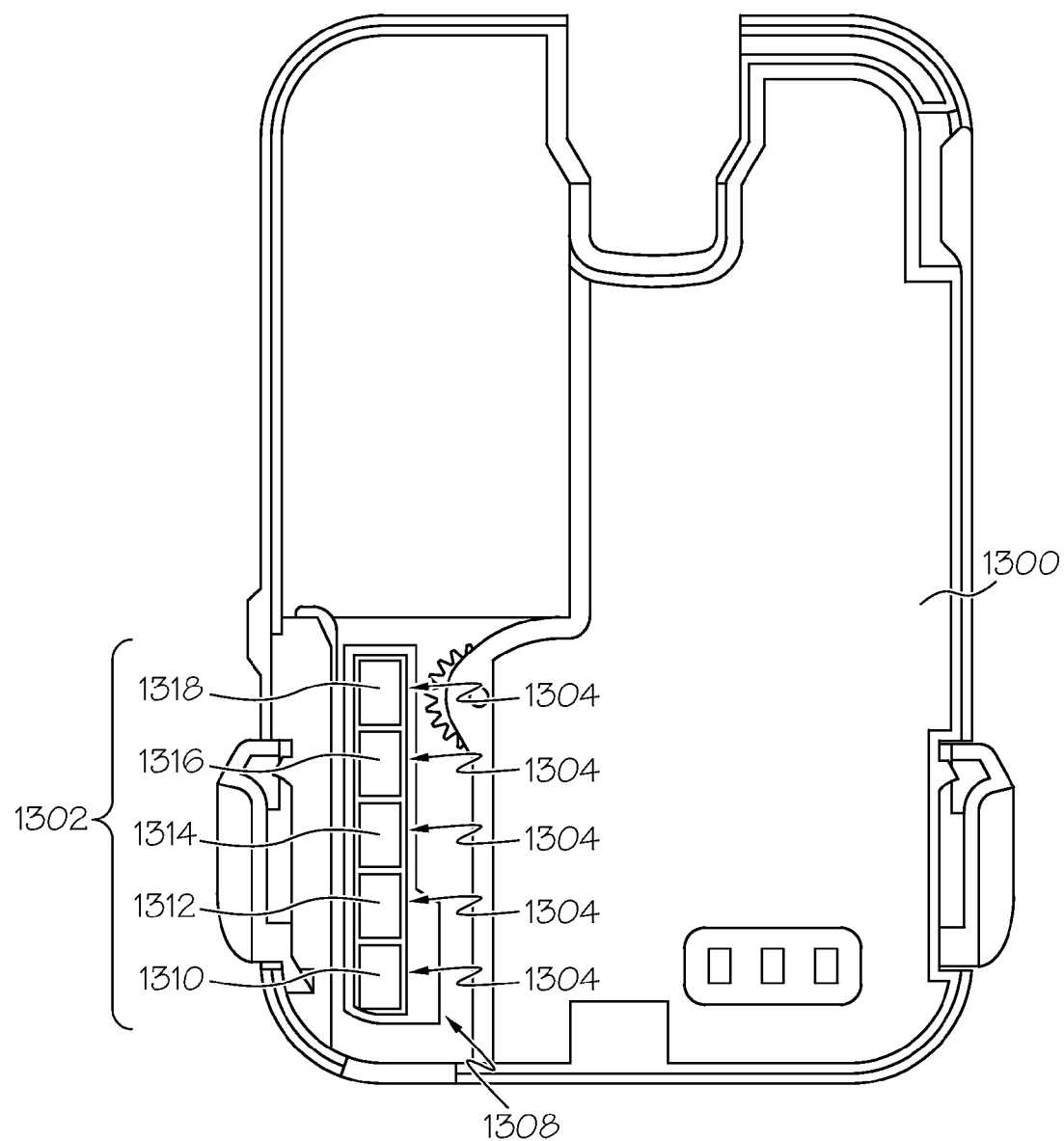
FIG. 13 is a plan view of an exemplary durable housing including a sensing arrangement comprised of a plurality of sensing elements that is suitable for use as the durable housing in the fluid infusion device of FIG. 2 in accordance with another embodiment.

FIG. 13 depicts another exemplary embodiment of a durable housing 1300 of a fluid infusion device suitable for use with the reservoir 800 of FIG. 8. The housing 1300 includes a sensing arrangement 1302 having a plurality of discrete sensing elements 1304 formed in (or on) a wall of the voided shaft portion 1308 so that the sensing elements 1304 are proximate to (or adjacent to) the shaft portion 802 of the reservoir 800 when the reservoir 800 is inserted in the housing 1300. It should be noted that although FIG. 13 depicts the sensing elements 1304 as being visible, in exemplary embodiments, a cover layer (similar to cover layer 910) may be provided overlying the sensing arrangement 1302 to retain the sensing arrangement 1302 within the durable housing 1300 and/or protect the sensing elements 1304 from environmental elements. The output of an individual sensing element 1304 indicates a discrete position of the shaft 810 and/or the detectable feature 804 with respect to the sensing arrangement 1302 and/or the housing 1300. For example, when the detectable feature 804 is aligned with and/or proximate the first sensing element 1310, the first sensing element 1310 may output an electrical signal (e.g., a voltage or current) that indicates the detectable feature 804 is aligned with and/or proximate the first sensing element 1310 while the remaining sensing elements 1304 output electrical signals that indicate the detectable feature 804 is not aligned with and/or proximate the remaining sensing elements 1304. In response to displacement of the shaft 810 that causes the detectable feature 804 to be aligned with and/or proximate a second sensing element 1312, the second sensing element 1312 outputs an electrical signal that indicates the detectable feature 804 is aligned with and/or proximate the second sensing element 1312 while the remaining sensing elements 1304 output electrical signals that indicate the detectable feature 804 is not aligned with and/or proximate the remaining sensing elements 1304. For example, when the detectable feature 804 is aligned with the first sensing element 1310, the first sensing element 1310 may output a logical high voltage that indicates the detectable feature 804 is aligned with the first sensing element 1310 and the second sensing element 1312 may output a logical low voltage that indicates the detectable feature 804 is not aligned with the second sensing element 1312 until the detectable feature 804 is aligned with the second sensing element 1312, at which point the second sensing element 1312 outputs a logical high voltage. Once the detectable feature 804 is no longer aligned with the first sensing element 1310, the outputs a logical low voltage indicating the detectable feature 804 is no longer aligned with the first sensing element 1310. It should be noted that in some embodiments, for improved resolution, the detectable feature 804 may be configured to overlap or otherwise be sensed by adjacent sensing elements 1304 concurrently, or alternatively, the sensing elements 1304 may be positioned or otherwise arranged so that the detectable feature 804 is capable of overlapping or otherwise being sensed by adjacent sensing elements 1304 concurrently. For example, both sensing arrangements 1310, 1312 may output a logical high voltage when the detectable feature 804 is aligned between the first sensing arrangement 1310 and the second sensing arrangement 1312, thereby indicating the detectable feature 804 is positioned between the sensing elements 1310, 1312.

As described above in the context of FIG. 12, in accordance with one or more embodiments, when the sensing arrangement 1170 is realized as sensing arrangement 1302, the control module 1102 implements a counter that counts the incremental rotations detected by the position sensor 1110 and is reset each time the detectable feature 804 passes from one sensing element 1304 to another. For example, the control module 1102 may reset the counter when the output signal from the second sensing element 1312 changes state (e.g., from logical low voltage to logical high voltage) and use the value of the counter to determine the position of the detectable feature 1180 relative to the second sensing element 1312 and/or the third sensing elements 1314, thereby improving the resolution of the measured shaft position.

In accordance with one embodiment, the sensing elements 1304 are realized as magnetic sensing elements, such as Hall effect sensors or the like, and the detectable feature 804 is realized as a magnet or another magnetic element formed on or in the shaft 810. In this regard, the magnetic field of the magnetic element 804 influences the state of the magnetic sensing elements 1304 based on the position of the magnetic element 804 relative to the magnetic sensing elements 1304, and thereby, the output electrical signals generated by the magnetic sensing elements 1304 are indicative of the relative position of the magnetic element 804 and/or shaft 810.

In accordance with another embodiment, the sensing elements 1304 are realized as an optical sensing element, such as a photodiode or another photodetector. In this regard, the detectable feature 804 may be realized as a reflective feature (e.g., a portion of reflective material, a mirror, or the like) or another optical feature that is detectable by the optical sensing elements 1304. In some embodiments, the sensing arrangement 1302 and/or sensing elements 1304 may also include a radiation source, such as a light-emitting diode (LED) or the like, that emits electromagnetic radiation that is directed towards the shaft 810 and/or shaft portion 802 and reflected by the optical feature 804 to the sensing element 1304 aligned with the optical feature 804. In some embodiments, the radiation source may emit a reference electromagnetic signal having one or more reference signal characteristics that is directed towards the optical feature 804, wherein the optical feature 804 modulates or otherwise modifies one or more signal characteristics of the reference signal to produce a modified signal that is reflected and sensed, measured, or otherwise received by the sensing element(s) 1304. In this regard, the optical feature 804 may be configured so that the signal characteristics of the reflected signal(s) sensed, measured, or otherwise received by the sensing element(s) 1304 may correspond to the position of the shaft 810. For example, the optical feature 804 may be provided along the length of the shaft 810 and configured so that the intensity of the reflected signal received by the sensing element 1318 proximate the barrel 806 increases as the shaft 810 and/or plunger 808 is displaced further into the barrel 806.

In accordance with yet another embodiment, the sensing elements 1304 are realized as optical sensing elements, wherein the optically detectable feature is provided on an interior of the guide portion 814 of the reservoir 800. For example, the interior wall of the guide portion 814 that faces the sensing arrangement 1302 when the reservoir 800 is provided in the housing 1300 may include one or more reflective features and/or other optical features that are detectable by the optical sensing elements 1304 via the cutout portion 818 as the as the shaft 810 and/or plunger 808 is displaced further into the barrel 806. For example, in accordance with one embodiment, the interior walls of the guide potion 814 include a reflective material provided thereon and the sensing arrangement 1302 may include one or more radiation sources to direct electromagnetic radiation into the interior of the guide portion 814 via the cutout portion 818, wherein the intensity of the electromagnetic signals reflected back to the sensing elements 1304 via the cutout portion 818 increases as the as the shaft 810 and/or plunger 808 is displaced further into the barrel 806 and exposes a greater portion of the reflective material on the interior of the guide portion 814 and allows a greater amount of electromagnetic radiation to be reflected back out of the guide portion 814.

Still referring to FIG. 13, in accordance with one embodiment, the interior of the guide portion 814 may include a single detectable feature at or near the end of the guide portion proximate the barrel 806 of the reservoir 800 that is detectable by the sensing element 1318 proximate the barrel region of the housing 1300 when the shaft 810 is at or near a fully depressed position within the barrel 806 of the reservoir 800, and is thereby utilized to detect or otherwise obtain a measured position of the shaft 810 corresponding to the plunger 808 being at or near a fully depressed position within the barrel 806. In such an embodiment, additional sensing elements 1310, 1312, 1314, 1316 need not be present inside the housing 1300. When the sensing element 1318 proximate the barrel region of the housing 1300 detect the detectable feature inside the guide portion 814, the control module 1102 may obtain or otherwise identify the measured shaft position as corresponding to the shaft 810, 1150 being at or near a fully depressed position within the barrel 806, and thereby determine that the remaining amount of fluid is less than the threshold amount and generate notification of a low fluid volume condition in a similar manner as described above.

Figure 14:
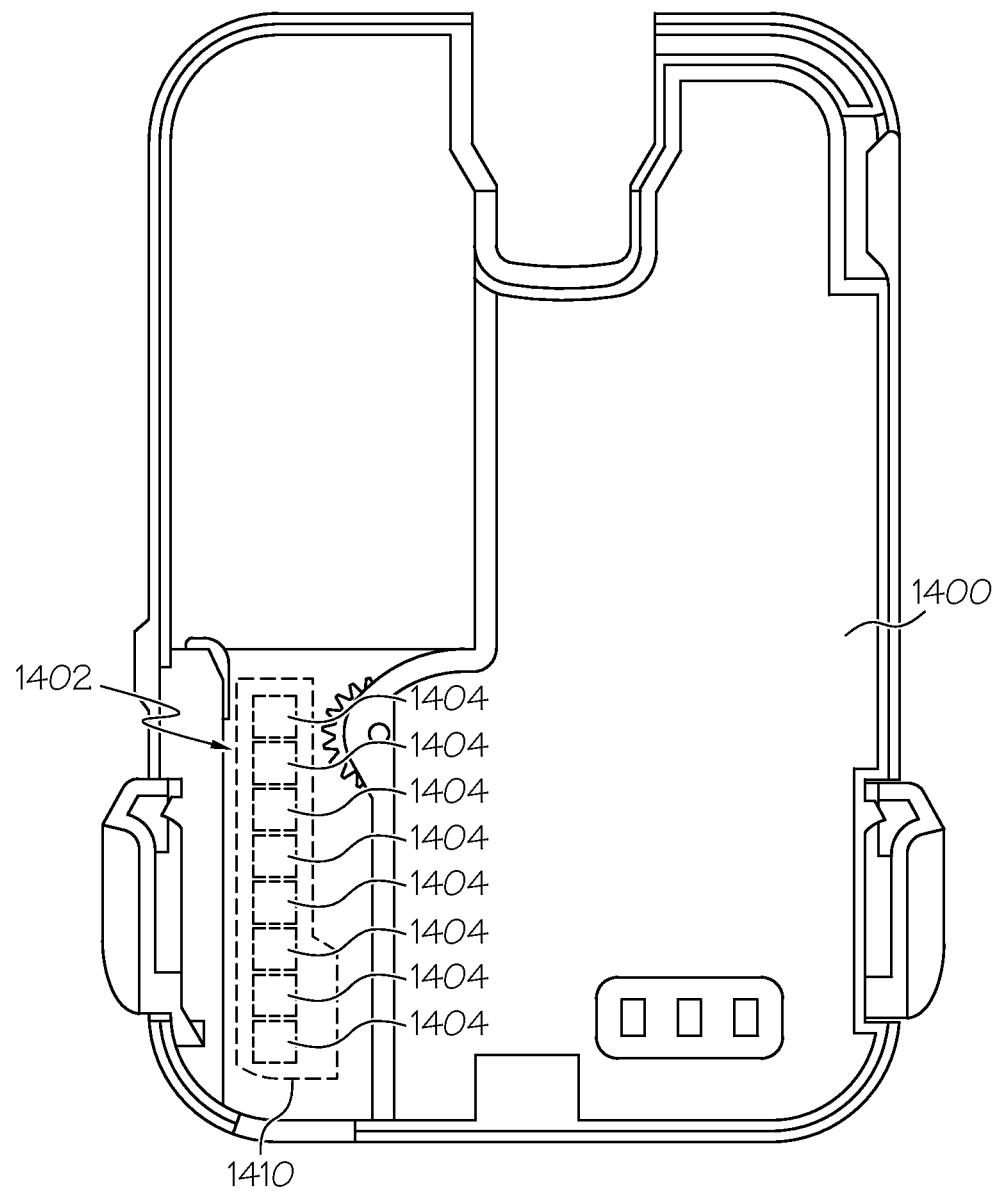
FIG. 14 is a plan view of an exemplary durable housing including a magnetic sensing arrangement suitable for use as the durable housing in the fluid infusion device of FIG. 2 in accordance with another embodiment.

Turning now to FIGS. 14-15, in accordance with one or more embodiments, a durable housing 1400 of a fluid infusion device includes a magnetic sensing arrangement 1402 including plurality of magnetic sensing elements 1404 suitable for use with a reservoir 1500 having a plurality of magnetic elements 1504, 1506, 1508 provided on its shaft 1502. In the illustrated embodiment, the magnetic sensors 1404 are realized as Hall effect sensors provided on a circuit board 1410 that is disposed within the housing 1400 and covered or otherwise contained by a cover layer.

In exemplary embodiments, the magnetic elements 1504, 1506, 1508 are realized as magnets having alternate polarity. For example, the magnetic element 1504 at the distal end of the shaft 1502 may have its magnetic north pole facing the magnetic sensing arrangement 1402, with the adjacent magnetic element 1506 having its magnetic south pole facing the magnetic sensing arrangement 1402 and the magnetic element 1508 closest to the barrel portion of the reservoir 1500 having its magnetic north pole facing the magnetic sensing arrangement 1402. In a similar manner as described above in the context of FIG. 13, the outputs of the magnetic sensors 1404 indicate the relative locations of the magnetic elements 1504, 1506, 1508 with respect to the sensing arrangement 1402 and/or housing 1400, which, in turn, indicates the position of the shaft 1502 with respect to the barrel portion of the reservoir 1500. In this regard, increasing the number of detectable features (e.g., magnetic elements 1504, 1506, 1508) combined with increasing the number of individual sensing elements (e.g., magnetic sensors 1404) improves the resolution for determining the shaft position.

FIG. 16 depicts another embodiment of a reservoir 1600 suitable for use with the housing 1400 of FIG. 14. The reservoir 1600 includes a single magnetic element 1604 on the shaft 1602 near the end of the shaft 1602 distal to the barrel of the reservoir 1600. The length of the magnetic element 1604 (e.g., the dimension of the magnetic element 1604 along the longitudinal axis of the shaft 1602) is greater than a sum of the length of an individual magnetic sensor 1404 and the distance between adjacent magnetic sensors 1404 so that the magnetic element 1604 concurrently overlaps or is otherwise aligned with multiple magnetic sensors 1404 when the reservoir 1600 is disposed within the housing 1400. As described above, a counter may be implemented that counts the incremental rotations detected by a position sensor and is reset each time the output of the next magnetic sensor 1404 closer to the barrel of the reservoir 1600 changes state to determine the shaft position.

Figure 17:
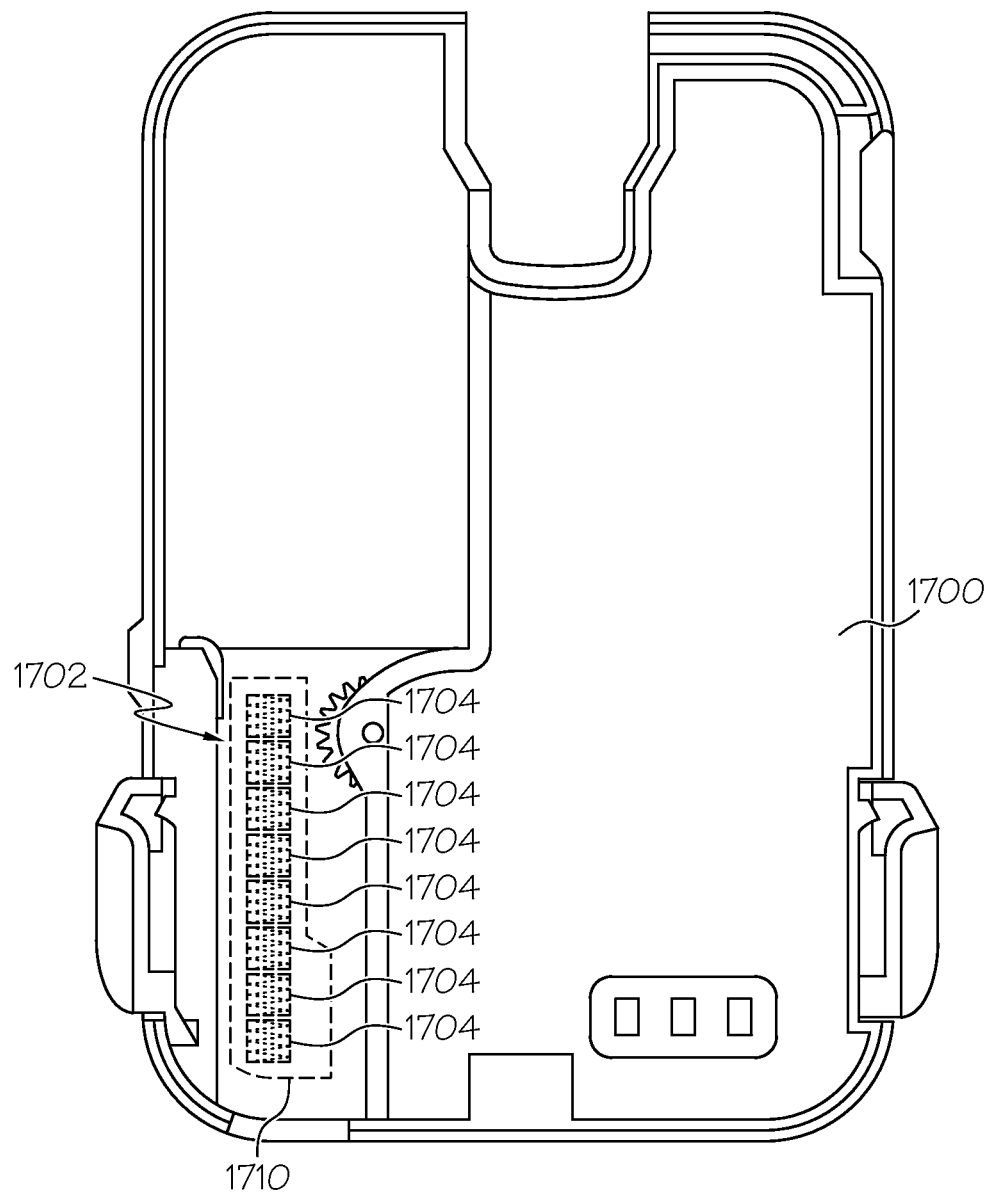
FIG. 17 is a plan view of an exemplary durable housing including an inductive sensing arrangement suitable for use as the durable housing in the fluid infusion device of FIG. 2 in accordance with another embodiment.
Figure 18:
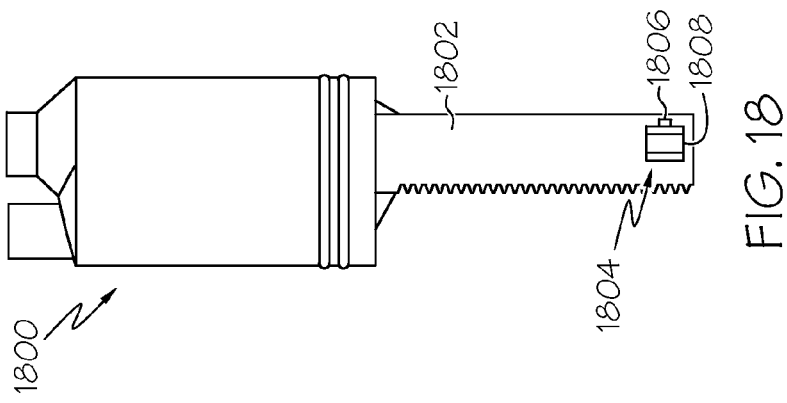
FIG. 18 is a plan view of an exemplary reservoir suitable for use with the durable housing of FIG. 17 in accordance with one embodiment.

Turning now to FIGS. 17-18, in accordance with one or more embodiments, a durable housing 1700 of a fluid infusion device includes an inductive sensing arrangement 1702 including plurality of inductive sensing elements 1704 suitable for use with a reservoir 1800 having a resonator 1804 provided on the end of its shaft 1802 that is distal to the barrel of the reservoir 1800. In the illustrated embodiment, the inductive sensing elements 1704 are realized as inductive sensors including one or more wires that zigzag relatively perpendicular to the longitudinal axis of the shaft 1802 of the reservoir 1800, wherein the inductive sensing elements 1704 are provided on a circuit board 1710 that is disposed within the housing 1700 and covered or otherwise contained by a cover layer. In exemplary embodiments, the resonator 1804 is affixed to the distal end of the shaft 1802 and includes an inductor 1806 that is affixed or otherwise mounted to a capacitor 1808, with the inductor 1806 and capacitor 1808 being configured electrically in series with one another to provide a resonant circuit. When the resonator 1804 overlaps or is otherwise aligned with an inductive sensing element 1704, the output of the inductive sensing element 1704 indicates the relative position of the resonator 1804, which, in turn, indicates the position of the shaft 1802.

Figure 20:
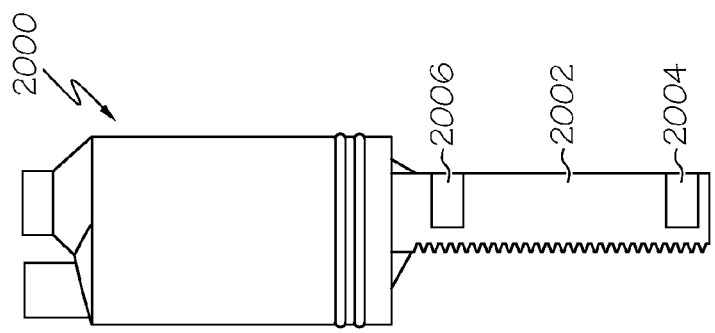
FIG. 20 is a plan view of an exemplary reservoir suitable for use with the durable housing of FIG. 19 in accordance with one embodiment.
Figure 19:
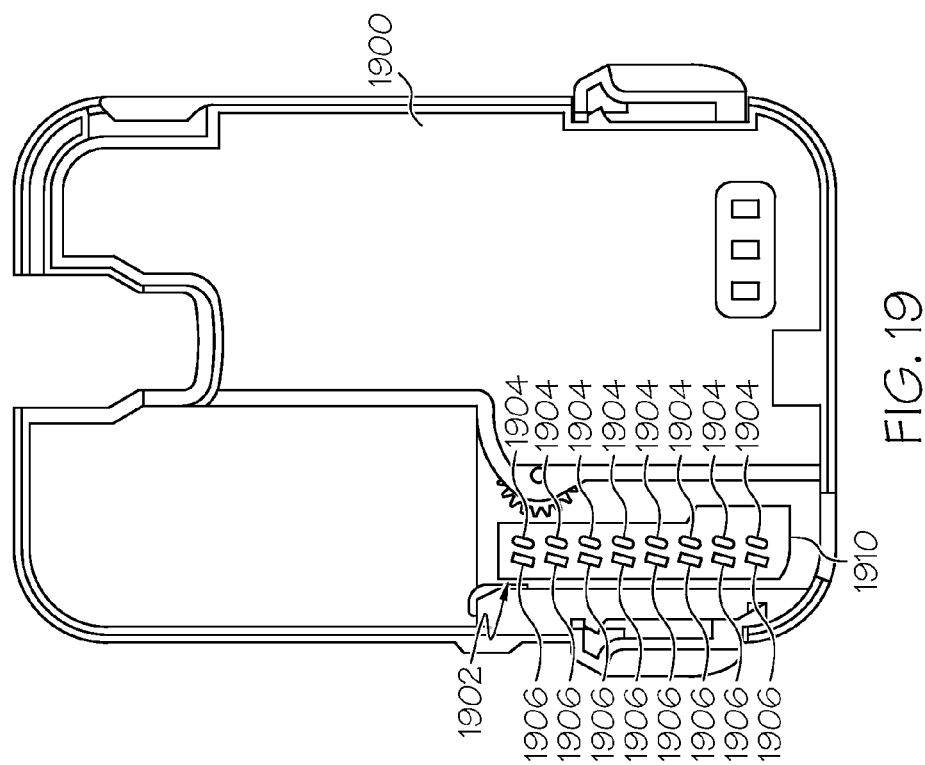
FIG. 19 is a plan view of an exemplary durable housing including an optical sensing arrangement that is suitable for use as the durable housing in the fluid infusion device of FIG. 2 in accordance with another embodiment.

Turning now to FIGS. 19-20, in accordance with one or more embodiments, a durable housing 1900 of a fluid infusion device includes an optical sensing arrangement 1902 suitable for use with a reservoir 2000 having a plurality of reflective elements 2004, 2006 provided on its shaft 2002. The optical sensing arrangement 1902 includes a plurality of light emitting elements 1904 and corresponding light detecting elements 1906 that are arranged along a longitudinal axis of a circuit board 1910 that corresponds to the longitudinal axis of the shaft 2002. The light emitting elements 1904 and the light detecting elements 1906 are oriented towards the shaft 2002 so that the light emitting elements 1904 direct light towards the shaft 2002 and the light detecting elements 1906 detect or otherwise sense the portion of the light reflected back towards the optical sensing arrangement 1902 by the reflective elements 2004, 2006 on the shaft 2002. In an exemplary embodiments, the light emitting elements 1904 are realized as light emitting diodes and the light detecting elements 1906 are realized as photodiodes which are mounted to a circuit board 1910 that is disposed within the housing 1900 and covered or otherwise contained by a transparent cover layer.

As illustrated in FIG. 20, in exemplary embodiments, a first reflective element 2004 is disposed near the end of the shaft 2002 that is distal to the barrel and the second reflective element 2006 is disposed near the end of the shaft 2002 that is proximate to the barrel. In this regard, when the reservoir 2000 is full, the reflective elements 2004, 2006 are aligned with or otherwise overlap the pairs of elements 1904, 1906 that are near the ends of the circuit board 1910. In accordance with one embodiment, when the optical sensing arrangement 1902 detects light reflected by both reflective elements 2004, 2006, a control system coupled to the optical sensing arrangement 1902 (e.g., control module 1102) determines that the reservoir 2000 is full. As described above, as the shaft 2002 is displaced in the axial direction toward and/or into the barrel, the reflective element 2004 at the distal end of the shaft 2002 overlaps one or more of the light detecting elements 1906, thereby providing an indication of the relative position of the shaft 2002.

Figure 22:
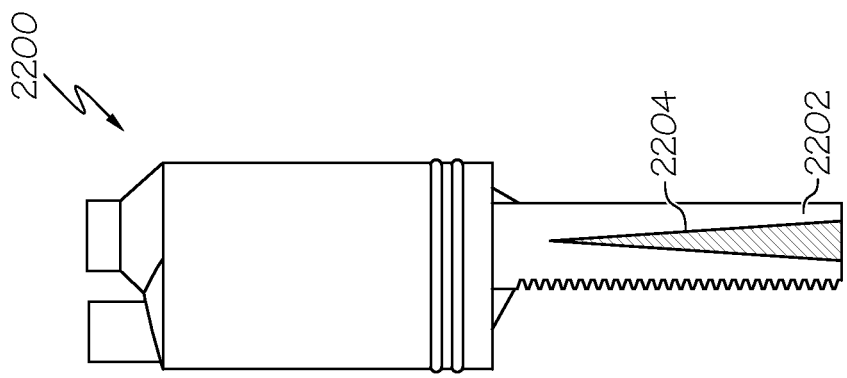
FIG. 22 is a plan view of an exemplary reservoir suitable for use with the durable housing of FIG. 21 in accordance with one embodiment.
Figure 21:
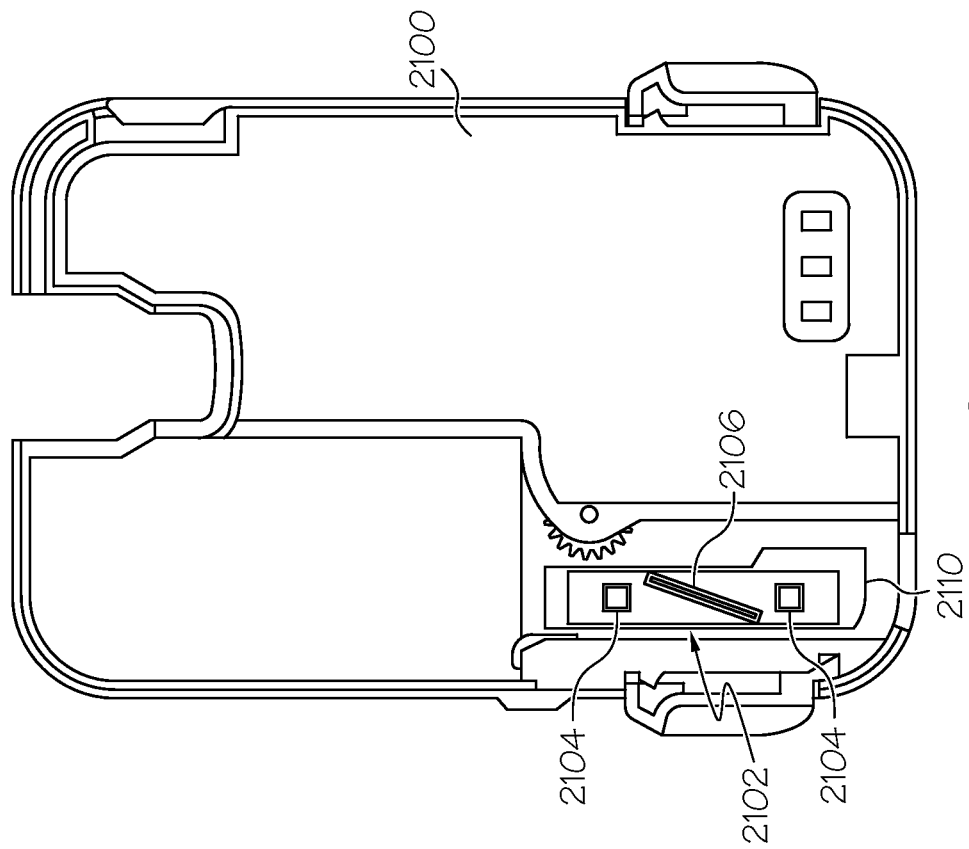
FIG. 21 is a plan view of another exemplary durable housing including an optical sensing arrangement that is suitable for use as the durable housing in the fluid infusion device of FIG. 2 in accordance with another embodiment.

Turning now to FIGS. 21-22, in accordance with one or more embodiments, a durable housing 2100 of a fluid infusion device includes an optical sensing arrangement 2102 suitable for use with a reservoir 2200 having an optically detectable pattern 2204 provided on its shaft 2202. The optical sensing arrangement 2102 includes a pair of light emitting elements 2104, such as light emitting diodes, disposed near opposing ends of an optical array sensor 2106, with the light emitting elements 2104 and optical array sensor 2106 being mounted or otherwise provided on a circuit board 2110 that is disposed within the housing 2100 and covered or otherwise contained by a transparent cover layer. The light emitting elements 2104 and the optical array sensor 2106 are oriented towards the shaft 2202 so that the light emitting elements 2104 direct light towards the shaft 2202 and the optical array sensor 2106 detects the pattern 2204 provided on the shaft 2202. In the illustrated embodiment, the pattern 2204 on the shaft 2202 is graduated so that the width of the pattern 2204 linearly increases towards the distal end of the shaft 2202. In this regard, the output of the optical array sensor 2106 is indicative of the width of the portion of the pattern 2204 that overlaps or is otherwise aligned with the optical array sensor 2106, and thus, is indicative of the relative position of the shaft 2202 with respect to the barrel of the reservoir 2200. In a similar manner as described above, a calibration procedure may be performed to correlate the output of the optical array sensor 2106 to the respective remaining amounts of fluid based on width of the portion of the pattern 2204 aligned with the optical array sensor 2106 at specific locations associated with shaft positions for known amounts of fluid remaining in the reservoir 2200. The relationship between the output of the optical array sensor 2106 and the remaining amounts of fluid may be interpolated and/or extrapolated to characterize the output generated by the optical array sensor 2106 as a function of the remaining amount of fluid in the reservoir, and a calibration table may be created that correlates values for remaining amounts of fluid in the reservoir and/or shaft positions to values of the output generated by the optical array sensor 2106 over the potential range of displacement for the shaft 2202.

FIG. 23 depicts another embodiment of a reservoir 2300 suitable for use with the housing 2100 of FIG. 21. The shaft 2302 of the reservoir 2300 includes a plurality of optically distinguishable portions 2304, 2306, 2308. In accordance with one embodiment, each portion 2304, 2306, 2308 of the shaft 2302 has a different color. For example, the portion 2308 of the shaft 2302 proximate the barrel may be colored red and the portion 2304 of the shaft 2302 distal to the barrel may be colored blue, with the intermediate portion 2306 of the shaft 2302 being colored green. In this regard, the relative position of the shaft 2302 (or the corresponding amount of fluid remaining in the reservoir 2300) may be determined based on the wavelength of light detected by the optical sensor 2106. For example, when the average wavelength detected by the optical sensor 2106 indicates the red portion 2308 of the shaft 2302 is primarily aligned with the optical sensor 2106, the amount of fluid remaining in the reservoir 2300 may be determined to be within a first range (e.g., greater than 150 units). Similarly, when the average wavelength detected by the optical sensor 2106 indicates the intermediate portion 2306 of the shaft 2302 is primarily aligned with the optical sensor 2106, the amount of fluid remaining in the reservoir 2300 may be determined to be within a second range (e.g., between 50 and 150 units), and when the average wavelength detected by the optical sensor 2106 indicates the end portion 2304 of the shaft 2302 is primarily aligned with the optical sensor 2106, the amount of fluid remaining in the reservoir 2300 may be determined to be within a third range (e.g., less than 50 units remaining). In this manner, the optically distinguishable portions 2304, 2306, 2308 provide a coarse measurement of the position of the shaft 2302.

The foregoing description may refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically. In addition, certain terminology may also be used in the herein for the purpose of reference only, and thus is not intended to be limiting. For example, terms such as "first", "second", and other such numerical terms referring to structures do not imply a sequence or order unless clearly indicated by the context.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. An infusion device, comprising:
a housing including a voided region to receive a reservoir, the voided region including a voided portion to receive a shaft portion including a shaft coupled to a plunger of the reservoir, the shaft portion comprising a detectable feature; and
a sensing arrangement proximate the voided portion to sense the detectable feature when the reservoir is inserted in the voided region, wherein resistance of the sensing arrangement is influenced by contact with the detectable feature, wherein:
the sensing arrangement comprises:
a bottom conductive layer comprising a substantially rigid material having a first conductive resistive carbon ink layer;
an upper conductive layer comprising a flexible material having a second conductive resistive carbon ink layer aligned with the first conductive resistive carbon ink layer on the bottom conductive layer; and
a spacer layer between the bottom conductive layer and the upper conductive layer, the bottom conductive layer and the upper conductive layer being spaced apart from one another by the spacer layer in the absence of a compressive force applied to the upper conductive layer; and
the resistance corresponds to a location where the upper conductive layer is compressed by the detectable feature.

2. The infusion device of claim 1, wherein the sensing arrangement comprises a resistive sensing arrangement having a variable resistance that is influenced by a location of the detectable feature with respect to the sensing arrangement.

3. The infusion device of claim 1, further comprising a flexible cover layer integrated with a wall of the voided portion, wherein:
the flexible cover layer overlies the upper conductive layer; and
the detectable feature contacts the flexible cover layer when the reservoir is provided within the voided region of the housing to compress the flexible cover layer and the upper conductive layer.

4. The infusion device of claim 3, wherein:
the detectable feature compresses the flexible cover layer and the upper conductive layer to cause the first conductive resistive carbon ink layer and the second conductive resistive carbon ink layer to contact one another.

5. The infusion device of claim 1, wherein the detectable feature comprises a protruding feature on the shaft.

6. The infusion device of claim 1, further comprising a control module coupled to the sensing arrangement to detect seating of the reservoir based on the electrical characteristic.

7. The infusion device of claim 1, further comprising a control module coupled to the sensing arrangement to obtain a measured position of the shaft using the sensing arrangement, estimate a remaining amount of fluid in the reservoir based on the measured position, and provide a low fluid notification when the remaining amount is less than a threshold value.

8. The infusion device of claim 1, further comprising a motor having a rotor coupled to the shaft, the shaft being displaced to deliver fluid from the reservoir in response to rotation of the rotor.

9. The infusion device of claim 8, further comprising:
a motor position sensor to measure an amount of rotation of the rotor; and
a control module coupled to the sensing arrangement and the motor position sensor to obtain a measured position of the shaft using the sensing arrangement, determine an expected position of the shaft based on the amount of rotation, and identify an anomalous condition based on a difference between the expected position and the measured position.

10. The infusion device of claim 9, wherein the control module identifies the anomalous condition based on the difference when an axial force aligned with the shaft is less than a threshold value and identifies an occlusion condition based on the difference when the axial force is greater than the threshold value.

11. An infusion device, comprising:
a housing including a voided region to receive a reservoir, the voided region including a voided portion to receive a shaft portion including a shaft coupled to a plunger of the reservoir, the shaft portion comprising a detectable feature; and
a sensing arrangement proximate the voided portion to sense the detectable feature when the reservoir is inserted in the voided region, wherein:
a resistance of the sensing arrangement is influenced by contact with the detectable feature; and
the sensing arrangement comprises:
a flexible cover layer integrated with a wall of the voided portion;
a bottom conductive layer;
an upper conductive layer; and
a spacer layer between the bottom conductive layer and the upper conductive layer, the bottom conductive layer and the upper conductive layer being spaced apart from one another by the spacer layer in the absence of a compressive force applied to the upper conductive layer;
the flexible cover layer overlies the upper conductive layer; and
the detectable feature contacts the flexible cover layer when the reservoir is provided within the voided region of the housing to compress the flexible cover layer and the upper conductive layer to provide the resistance corresponding to a location where the flexible cover layer and the upper conductive layer are compressed by the detectable feature.

12. The infusion device of claim 11, wherein:
the bottom conductive layer comprises a substantially rigid material having a first conductive resistive carbon ink layer;
the upper conductive layer comprises a flexible material having a second conductive resistive carbon ink layer aligned with the first conductive resistive carbon ink layer on the bottom conductive layer; and
the detectable feature compresses the flexible cover layer and the upper conductive layer to cause the first conductive resistive carbon ink layer and the second conductive resistive carbon ink layer to contact one another.

13. The infusion device of claim 11, wherein the detectable feature comprises a protruding feature on the shaft.

14. The infusion device of claim 11, further comprising a control module coupled to the sensing arrangement to detect seating of the reservoir based on the electrical characteristic.

15. The infusion device of claim 11, further comprising a control module coupled to the sensing arrangement to obtain a measured position of the shaft using the sensing arrangement, estimate a remaining amount of fluid in the reservoir based on the measured position, and provide a low fluid notification when the remaining amount is less than a threshold value.

16. The infusion device of claim 11, further comprising a motor having a rotor coupled to the shaft, the shaft being displaced to deliver fluid from the reservoir in response to rotation of the rotor.

17. The infusion device of claim 16, further comprising:
a motor position sensor to measure an amount of rotation of the rotor; and
a control module coupled to the sensing arrangement and the motor position sensor to obtain a measured position of the shaft using the sensing arrangement, determine an expected position of the shaft based on the amount of rotation, and identify an anomalous condition based on a difference between the expected position and the measured position.

18. The infusion device of claim 17, wherein the control module identifies the anomalous condition based on the difference when an axial force aligned with the shaft is less than a threshold value and identifies an occlusion condition based on the difference when the axial force is greater than the threshold value.

19. A method of operating an infusion device to deliver fluid from a reservoir including a plunger coupled to a shaft such that displacement of the shaft results in displacement of the plunger, the infusion device including a sensing arrangement to sense a detectable feature on the shaft, the method comprising:
operating a motor having a rotor coupled to the shaft to displace the shaft in response to rotation of the rotor and deliver the fluid from the reservoir;
obtaining a measured shaft position based at least in part on an electrical output signal provided by the sensing arrangement that is indicative of the detectable feature contacting the sensing arrangement, wherein the electrical output signal corresponds to a location of the detectable feature contacting the sensing arrangement;
determining a remaining amount of fluid in the reservoir based on the measured shaft position; and
providing a low fluid notification when the remaining amount is less than a threshold value, wherein:
a resistance of the sensing arrangement is influenced by contact with the detectable feature; and
the sensing arrangement comprises:
a flexible cover layer integrated with a wall of the voided portion;
a bottom conductive layer;
an upper conductive layer; and
a spacer layer between the bottom conductive layer and the upper conductive layer, the bottom conductive layer and the upper conductive layer being spaced apart from one another by the spacer layer in the absence of a compressive force applied to the upper conductive layer;
the flexible cover layer overlies the upper conductive layer; and
the detectable feature contacts the flexible cover layer when the reservoir is provided within the voided region of the housing to compress the flexible cover layer and the upper conductive layer to provide the resistance corresponding to a location where the flexible cover layer and the upper conductive layer are compressed by the detectable feature.

20. The method of claim 19, wherein the sensing arrangement comprises a resistive sensing arrangement having a variable resistance that is influenced by the position of the detectable feature with respect to the sensing arrangement.

* * * * *